US009568470B2

United States Patent
Kurosawa et al.

(10) Patent No.: US 9,568,470 B2
(45) Date of Patent: Feb. 14, 2017

(54) METHOD FOR INCREASING THE SENSITIVITY OF IMMUNOASSAY SYSTEM THROUGH PRETREATMENT OF URINE WITH DENATURANT

(71) Applicant: DENKA SEIKEN CO., LTD, Chuo-ku, Tokyo (JP)

(72) Inventors: Hiroyuki Kurosawa, Niigata (JP); Yoshiaki Hirayama, Niigata (JP)

(73) Assignee: Denka Seiken Co., Ltd., Tokyo (JP)

( * ) Notice: Subject to any disclaimer, the term of this patent is extended or adjusted under 35 U.S.C. 154(b) by 0 days.

(21) Appl. No.: 14/437,568

(22) PCT Filed: Oct. 23, 2013

(86) PCT No.: PCT/JP2013/078681
§ 371 (c)(1),
(2) Date: Apr. 22, 2015

(87) PCT Pub. No.: WO2014/065312
PCT Pub. Date: May 1, 2014

(65) Prior Publication Data
US 2015/0285791 A1 Oct. 8, 2015

(30) Foreign Application Priority Data
Oct. 23, 2012 (JP) ................................. 2012-233891

(51) Int. Cl.
*G01N 33/00* (2006.01)
*G01N 33/53* (2006.01)

(52) U.S. Cl.
CPC ..... *G01N 33/5306* (2013.01); *G01N 2333/705* (2013.01)

(58) Field of Classification Search
CPC .................. G01N 33/5306; G01N 2333/705; G01N 33/00; G01N 33/53
See application file for complete search history.

(56) References Cited

U.S. PATENT DOCUMENTS

| 5,888,827 A * | 3/1999 | Kayahara ................. C12Q 1/32 |
| | | 252/408.1 |
| 7,745,145 B2 * | 6/2010 | Schmitt .................... G01N 1/30 |
| | | 435/7.1 |
| 2003/0022160 A1 * | 1/2003 | Maes ....................... C12Q 1/04 |
| | | 435/5 |
| 2003/0129679 A1 * | 7/2003 | Siddiqi ............ G01N 33/57449 |
| | | 435/7.32 |
| 2004/0058395 A1 | 3/2004 | Hara |
| 2005/0089948 A1 * | 4/2005 | Kocagoz .................. G01N 1/40 |
| | | 435/34 |
| 2005/0227225 A1 * | 10/2005 | Krevolin ............... A61L 2/0082 |
| | | 435/5 |
| 2007/0015911 A1 * | 1/2007 | Warder .............. G01N 33/6851 |
| | | 530/414 |
| 2010/0233738 A1 | 9/2010 | Hara et al. |
| 2012/0040374 A1 | 2/2012 | Saito et al. |
| 2012/0058489 A1 | 3/2012 | Saito et al. |

FOREIGN PATENT DOCUMENTS

| EP | 0 566 205 A1 | 10/1993 |
| EP | 1 083 428 A2 | 3/2001 |
| JP | 07-27764 A | 1/1995 |
| JP | 2001-124779 A | 5/2001 |
| JP | 2001-289850 A | 10/2001 |
| WO | WO 02/37099 A1 | 5/2002 |
| WO | WO 2009/041577 A1 | 4/2009 |
| WO | WO 2010/126043 A1 | 11/2010 |
| WO | WO 2010/126055 A1 | 11/2010 |

OTHER PUBLICATIONS

Christensen et al., "Essential Role of Megalin in Renal Proximal Tubule for Vitamin Homeostasis," J. Am. Soc. Nephrol., 1999, 10:2224-2236.
Jung et al., "Immortalized rat proximal tubule cells produce membrane bound and soluble megalin," Kidney International, 1998, 53:358-366.
Zheng et al., "Organ Distribution in Rats of Two Members of the Low-density Lipoprotein Receptor Gene Family, Gp330 and LRP/α2MR, and the Receptor-associated Protein (RAP)," The Journal of Histochemistry and Cytochemistry, 1994, 42(4);531-542.

* cited by examiner

*Primary Examiner* — Gary W Counts
(74) *Attorney, Agent, or Firm* — Foley & Lardner LLP

(57) ABSTRACT

An object of the present invention is to provide a method for increasing the sensitivity of an immunoassay system. In order to achieve the object, the present inventors have discovered that the sensitivity of an immunoassay system can be increased by pretreating urine and thus have completed the present invention.

6 Claims, 1 Drawing Sheet

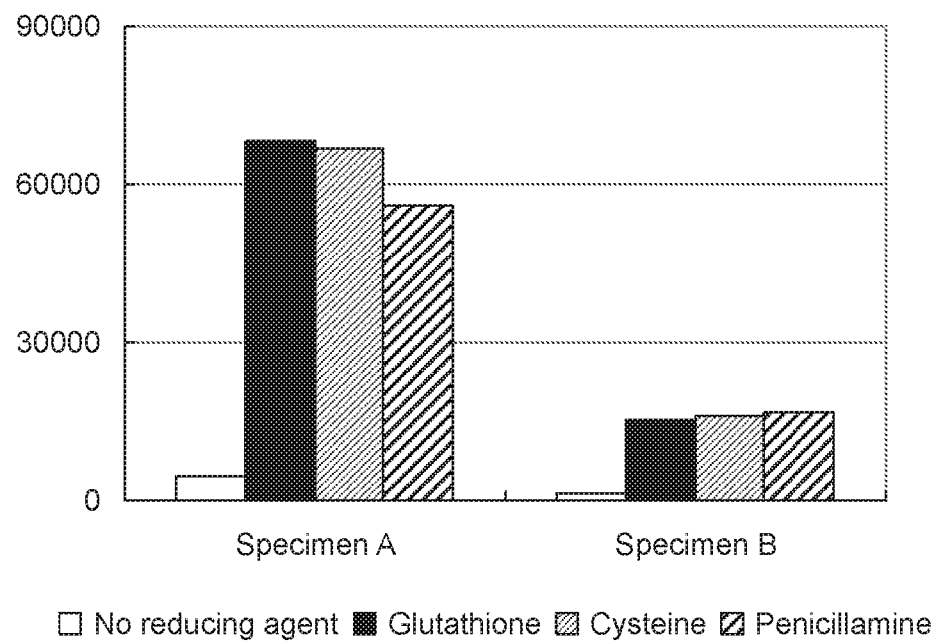

METHOD FOR INCREASING THE SENSITIVITY OF IMMUNOASSAY SYSTEM THROUGH PRETREATMENT OF URINE WITH DENATURANT

CROSS-REFERENCE TO RELATED APPLICATIONS

This application is a National Stage application of PCT/JP2013/078681, filed Oct. 23, 2013, which claims priority from Japanese application JP 2012-233891, filed Oct. 23, 2012.

TECHNICAL FIELD

The present invention relates to a method for increasing the sensitivity of an immunoassay system through pretreatment of urine.

BACKGROUND ART

Measuring urinary proteins is useful for diagnosing various diseases and symptoms. When these proteins are measured, they are highly diluted in buffer and then used. However, it is difficult to detect some proteins that have recently been attracting attention because of their low concentrations in urine, if these proteins are highly diluted in a conventional manner.

An example of a substance related to renal diseases is urinary megalin. Convenient means for testing renal disorders, which comprise measuring urinary megalin, are disclosed (Patent Documents 1 and 2).

Megalin also known as Glycoprotein 330 (gp330) or Low Density Lipoprotein (LDL)-receptor relate protein 2 (LRP2) is a glycoprotein having a molecular weight of about 600 kDa, which is expressed in renal proximal tubular epithelial cells (Non-patent Documents 1 and 2).

As a result of cell culture experiments using renal proximal tubular epithelial cells, the presence of two types of megalin, membrane-bound full length megalin and Soluble-Form megalin (fragment containing the extracellular region) lacking the intracellular region, is known (Non-patent Document 3). A method for measuring urinary full length human megalin, the extracellular region thereof, and the intracellular region thereof has also been reported (Patent Document 3).

Since urinary megalin concentration is low, high-degree dilution makes the measurement of urinary megalin difficult. Urinary megalin should be measured without high-degree dilution or measured with increased sensitivity. A measurement method not involving high-degree dilution is already known (Patent Document 4), but no method that involves increasing sensitivity exists. Development of a method for increasing sensitivity and the combined use thereof with the method of Patent Document 4 make it possible to detect urinary proteins with even lower concentrations. This leads to early disease detection and thus is advantageous in terms of medical economy.

PRIOR ART DOCUMENTS

Patent Documents

Patent Document 1: International publication WO2002/037099
Patent Document 2: International publication WO2010/126055
Patent Document 3: International publication WO2010/126043
Patent Document 4: International publication WO2009/041577

Non-Patent Documents

Non-patent Document 1: Christensen E. I., Willnow T. E. (1999) J. Am. Soc. Nephrol. 10, 2224-2236
Non-patent Document 2: Zheng G, McCluskey R. T. et al. (1994) J. Histochem. Cytochem. 42, 531-542
Non-patent Document 3: Flavia F. J., Julie R. I. et al. (1998) Kidney. International. 53, 358-366

SUMMARY OF THE INVENTION

Problem to be Solved by the Invention

An object of the present invention is to provide a method for increasing the sensitivity of an immunoassay system.

Means for Solving the Problem

To achieve the above object, the present inventors have discovered that the sensitivity of an immunoassay system that is, assay sensitivity for urinary proteins to be measured can be increased by adding 1 type or 2 types of compound comprising a reducing agent, a chaotropic reagent, and a surfactant to urine for pretreatment thereof using these compounds. Thus, the present inventors have completed the present invention.

Specifically, the present invention is as follows.

[1] An immunoassay method for measuring a protein in a urine specimen, comprising pretreating a urine specimen by mixing the urine specimen with a denaturant, and then performing immunoassay, thereby improving assay sensitivity for the protein.
[2] The immunoassay method of [1], wherein a urinary concentration of the protein is low.
[3] The immunoassay method of [1] or [2], wherein the denaturant is a reducing agent.
[4] The immunoassay method of [3], comprising pretreating a urine specimen by adding a reducing agent to the urine specimen at a concentration ranging from 0.0127 mM to 64 mM.
[5] The immunoassay method of [3] or [4], wherein the reducing agent is glutathione.
[6] The immunoassay method of [5], comprising pretreating a urine specimen by adding glutathione to the urine specimen at a concentration ranging from 0.0127 mM to 13 mM.
[7] The immunoassay method of [3] or [4], wherein the reducing agent is cysteine.
[8] The immunoassay method of [7], comprising pretreating a urine specimen by adding cysteine to the urine specimen at a concentration ranging from 0.0625 mM to 16 mM.
[9] The immunoassay method of [3] or [4], wherein the reducing agent is penicillamine.
[10] The immunoassay method of [9], comprising pretreating a urine specimen by adding penicillamine to the urine specimen at a concentration ranging from 0.0625 mM to 64 mM.
[11] The immunoassay method of [1] or [2], whereby pretreatment is performed with a combination of 2 types of denaturant.
[12] The immunoassay method of [11], wherein the denaturants combined herein are a reducing agent and a chaotropic reagent.
[13] The immunoassay method of [12], wherein the reducing agent is glutathione and the chaotropic reagent is urea.
[14] The immunoassay method of [12], wherein the reducing agent is cysteine and the chaotropic reagent is urea.

[15] The immunoassay method of [12], wherein the reducing agent is penicillamine and the chaotropic reagent is urea.
[16] The immunoassay method of [11], wherein the denaturants combined herein are a reducing agent and a surfactant.
[17] The immunoassay method of [16], wherein the reducing agent is glutathione and the surfactant is sodium n-dodecylbenzenesulfonate (SDBS).
[18] The immunoassay method of [16], wherein the reducing agent is cysteine and the surfactant is sodium n-dodecylbenzenesulfonate (SDBS).
[19] The immunoassay method of [16], wherein the reducing agent is penicillamine and the surfactant is sodium n-dodecylbenzenesulfonate (SDBS).
[20] The immunoassay method of any one of [13] to [15], comprising pretreating a urine specimen by adding urea to the urine specimen at a concentration ranging from 5 mM to 320 mM.
[21] The immunoassay method of any one of [17] to [19], comprising pretreating a urine specimen by adding sodium n-dodecylbenzenesulfonate (SDBS) to the urine specimen at a concentration ranging from 1.43 mM to 5.74 mM.

This description includes all or part of the contents as disclosed in the description and/or drawings of Japanese Patent Application No. 2012-233891, which is a priority document of the present application.

Effect of the Invention

The present invention makes it possible to measure a urinary protein with a low concentration, which has been difficult to measure by conventional immunoassay methods using urine specimens.

BRIEF DESCRIPTION OF THE DRAWINGS

FIG. 1 shows the results of comparing the measured values of urinary megalin in the presence and absence of reducing agents.

MODES FOR CARRYING OUT THE INVENTION

The present invention will be described in detail as follows.

The present invention is a method for increasing the assay sensitivity of an immunoassay system for measuring urinary proteins using urine as a specimen through pretreatment of urine.

Urine as a specimen may be obtained from any subject. Specifically, urine collected from a healthy subject and urine collected from a subject with a specific disease or a subject in a specific health condition can all be used herein. Any method for collecting urine may be employed herein. Morning urine or spot urine is preferably used. In addition, the amount of urine required for the method of the present invention ranges from about 10 μL, to 200 μL.

Examples of urinary proteins to be measured include, but are not limited to, megalin, podocalyxin, β2-microglobulin, α1-microglobulin, N-acetyl-β-D-glucosaminidase, Neutrophil gelatinase-associated lipocalin, Kidney Injury Molecule-1, midkine, L type fatty acid binding protein, interleukin 18, and type IV collagen. Urinary proteins may be proteins that could be discovered in the future.

These proteins are related to specific diseases and specific health conditions, the concentrations of which in urine are increased or decreased when a subject has a specific disease or a subject has a specific health condition.

For example, megalin, podocalyxin, β2-microglobulin, α1-microglobulin, N-acetyl-β-D-glucosaminidase, Neutrophil gelatinase-associated lipocalin, Kidney Injury Molecule-1, midkine, L type fatty acid binding protein, interleukin18, and type IV collagen are proteins related to diseases with renal dysfunction. If highly sensitive measurement thereof becomes possible, early detection of renal disorder becomes possible, which is significantly advantageous for patients.

The concentrations of some of these proteins are so low in urine that the assay sensitivity therefor in general immunoassay is also low and these proteins are difficult to measure. According to the method of the present invention, the assay sensitivity for such proteins having low concentrations in urine can be increased when the proteins are measured by an immunoassay system using urine specimens. Hence, proteins having low concentrations in urine can be precisely determined.

A measurement system, the assay sensitivity of which can be increased by the method of the present invention, is a measurement system using antigen-antibody reaction with an antibody against a protein to be measured.

Urine can be pretreated by adding and mixing a treatment solution with which collected urine can be treated as desired. In the present invention, the pretreatment of a urine specimen means that such a treatment solution is added to and mixed with a urine specimen, so as to perform particular treatment of the urine specimen or a protein to be measured in the urine specimen with the use of the treatment solution.

Examples of treatment include pH adjustment for urine, masking of urinary sediment, as well as solubilization or denaturation of urinary proteins. Examples of a treatment solution include treatment solutions with which pH adjustment of urine, masking of urinary sediment, as well as solubilization or denaturation of urinary proteins can be performed. Preferably, a treatment solution with which urinary proteins can be solubilized or denatured is used.

An example of such a treatment solution is a solution prepared by adding a denaturant to a buffer. A buffer that is generally used for immunoassay can be used herein. A phosphate buffer, tris buffer, or the like having about pH6-9 can be used.

In the present invention, a denaturant is a compound that causes protein denaturation, or protein solubilization. Examples thereof include a surfactant, a chaotropic reagent, and a reducing agent.

Examples of a surfactant include anion-based surfactants, cation-based surfactants, ampholytic surfactants, and non-ionicsurfactants. Preferably, anionic surfactants are used. Specific examples thereof include carboxylic acid type, sulfonic acid type, sulfuric acid ester type, and phosphoric ester type surfactants. Further specific examples thereof include sodium n-dodecylbenzenesulfonate (SDBS), sodium dodecyl sulfate (SDS), sodium octanoate, sodium decanoate, sodium laurate, sodium myristate, sodium palmitate, sodium stearate, perfluorononanoic acid, sodium N-lauroyl sarcosinate, α-sulfo fatty acid methyl ester salt, sodium 1-hexanesulfonate, sodium 1-octanesulfonate, sodium 1-decanesulfonate, sodium 1-dodecanesulfonate, perfluorobutanesulfonic acid, sodium toluenesulfonate, sodium cumenesulfonate, sodium octylbenzenesulfonate, sodium naphthalene sulfonate, disodium naphthalene disulfonate, trisodium naphthalene trisulfonate, sodium butylnaphthalenesulfonate, sodium myristyl sulfate, sodium laureth sulfate, sodium polyoxyethylene alkyl phenol sulfonate, ammonium lauryl sulfate, lauryl phosphoric acid, sodium lauryl phosphate, and potassium lauryl phosphate.

The term "chaotropic reagent" refers to a substance that increases the water solubility of hydrophobic molecules, and decreases hydrophobic interaction. Examples of a chaotropic reagent include guanidine thiocyanate, sodium perchlorate, sodium thiocyanide, guanidine hydrochloride, urea, and iodide ions. Any known chaotropic reagent may be used herein.

Examples of a reducing agent include glutathione, cysteine, penicillamine, tris(2-carboxyethyl) phosphine, aminoethanethiol, mercaptopropanesulfonic acid, mercaptosuccinic acid, thiolactic acid, mercaptopyrimidine, mercaptoethanol, and dithiothreitol. Any known reducing agent may be used herein.

Moreover, 1 type or a combination of 2 or more types of the above denaturant may be used herein. Examples of a combination include a combination of at least 1 type of reducing agent and at least 1 type of chaotropic reagent, a combination of at least 1 type of reducing agent and at least 1 type of surfactant, and a combination of at least 1 type of chaotropic reagent and at least 1 type of surfactant. Also, 2 or more types of reducing agent alone, 2 or more types of chaotropic reagent alone, and 2 or more types of surfactant alone can be used herein.

The final concentrations of a surfactant, a chaotropic reagent and a reducing agent in a urine specimen, when they are added as a treatment solution to the urine specimen can be determined as appropriate. For example the final concentrations may be determined from concentrations ranging from 0.01 mM to 500 mM. When a denaturant is a reducing agent, the reducing agent may be added at a concentration between 0.0127 mM and 64 mM, for example.

Moreover, concentrations of specific substances to be used as a surfactant, a chaotropic reagent, and a reducing agent, and specific combinations and concentrations thereof are as follows. When glutathione that is a reducing agent is used as a denaturant, the concentration thereof in urine ranges from 0.01 mM to 20 mM, preferably from 0.01 mM to 15 mM, further preferably from 0.01 mM to 13 mM, and particularly preferably from 0.0127 mM to 13 mM. When cysteine that is a reducing agent is used as a denaturant, the concentration thereof in urine ranges from 0.05 mM to 25 mM, preferably from 0.05 mM to 20 mM, further preferably from 0.01 mM to 16 mM, and particularly preferably from 0.0625 mM to 16 mM. When penicillamine that is a reducing agent is used as a denaturant, the concentration thereof in urine ranges from 0.05 mM to 100 mM, preferably from 0.05 mM to 75 mM, further preferably from 0.05 mM to 64 mM, and particularly preferably from 0.0625 mM to 64 mM.

Moreover, when the above reducing agent and urea that is a chaotropic reagent or sodium n-dodecylbenzenesulfonate (SDBS) that is a surfactant are used in combination, for example, 1 mM to 1000 mM, preferably 5 mM to 500 mM, and further preferably 5 mM to 320 mM urea can be used in combination with a reducing agent having a concentration within the above concentration range, for example. Alternatively, 0.5 mM to 20 mM, preferably 1 mM to 10 mM, and further preferably 1.43 mM to 5.74 mM SDBS can be used in combination with a reducing agent having a concentration within the above concentration range.

A specific example of a treatment solution is a solution of 400 mM Tris-HCl (pH8.0) containing 40 mM EDTA, 2% (Vol./Vol.) Triton™ X-100 (octylphenol ethoxylate), and 1.625 mM glutathione. Such a treatment solution is added to and mixed with the same volume of a urine specimen, so that a urine sample solution can be obtained. For example, 500 µL of a treatment solution is added to and mixed with 50 µL of a urine specimen, and then the mixture can be used.

Through treatment of a urine specimen with the above denaturant, the physicochemical properties of an antigen protein (to be measured) in urine are altered, the frequency of contact of the antibody to the protein is increased, and thus antigen-antibody reaction is accelerated. Furthermore, treatment with the above denaturant can cause a decrease in non-specific binding. As a result, assay sensitivity for a protein in urine can be increased. Here, the expression, "assay sensitivity for a protein in urine is increased" means that the intensity of signals generated based on the presence of the relevant protein in an immunoassay system is increased, and at the same time background signals are decreased, so as to increase the intensity of signals generated based on the presence of the above relevant protein. An immunoassay system measures an antigen protein that is present in a sample by binding an antibody labeled with a labeling substance to an antigen protein to be measured, measuring signals generated from the labeling substance, and thus detecting the protein bound to the antibody. The term "signals" refers to signals that are generated from such a labeling substance. Examples of a labeling substance include a fluorescent substance, an enzyme, heavy metal, and a radiative isotopic element.

The present invention is an immunoassay method for measuring a protein in a urine specimen, which comprises pretreating a urine specimen by mixing a denaturant with the urine specimen for immunoassay, thereby improving the assay sensitivity for the above protein. The immunoassay method for measuring a protein in a urine specimen also increases the sensitivity of an immunoassay system; that is, assay sensitivity for a protein by mixing a denaturant with the urine specimen for pretreatment of the urine specimen, followed by immunoassay.

A measurement method employed when a protein to be measured is megalin is described in detail as follows. All proteins other than megalin can be measured based on the megalin measurement method.

Various methods can be used for detecting megalin from a urine sample solution. An example of a method for detecting megalin is an immunological technique. An immunological technique can be performed by immunostaining methods (including a fluorescent antibody technique, an enzyme antibody method, a heavy metal-labeled antibody method, and a radioisotope-labeled antibody method), methods using a combination of separation by electrophoresis and detection using fluorescence, enzyme, and radioisotope etc., (including Western blot method and fluorescence two-dimensional electrophoresis), an enzyme-linked immunosorbent assay (ELISA) method, a dot blotting method, a latex agglutination method (LA: Latex Agglutination-Turbidimetric Immunoassay), immunochromatography method, or the like. Preferably, ELISA methods or LA methods are employed. Among ELISA methods, a sandwich method is preferably employed from a quantitative viewpoint. In the case of a sandwich method, a urine sample solution is added to a microtiter plate to which an anti-megalin antibody has been immobilized for antigen-antibody reaction to take place, an enzyme-labeled anti-megalin antibody is further added for an antigen-antibody reaction to take place, washing is performed, the resultant is reacted with an enzyme substrate for color development, absorbance is measured, and thus urinary megalin is detected and the concentration of urinary megalin can be calculated from the measured value. Moreover, an antigen-antibody reaction is performed using a fluorescence-labeled anti-megalin antibody, and then fluorescence can be measured.

An anti-megalin antibody that is used in an immunological technique may be an antibody with which human megalin can be detected. An anti-megalin antibody that is used in the present invention may be a known antibody or an antibody that could be developed in the future. Examples of an anti-megalin antibody include, but are not particularly limited to: a monoclonal antibody, a polyclonal antibody, a chimeric antibody, a humanized antibody, and fragments thereof with binding activity. These antibodies may be labeled with enzymes or fluorescent dyes. In addition, 2 or more types of anti-megalin antibody may be used. Two (2)

or more types of anti-megalin antibody are used for the above sandwich method, and are preferably antibodies that recognize epitopes differing from each other.

EXAMPLES

The present invention is described in detail with reference to examples of the present invention. However, the present invention is not limited thereto and various applications of the present invention are feasible within the technical idea of the present invention.

Example 1

Comparison of Assay Sensitivity for Urinary Megalin Between the Presence and the Absence of Reducing Agent (1) Method for Measuring Urinary Megalin Using Urine not Subjected to Reduction Treatment A fragment (the extracellular region of megalin) containing human megalin extracellular region was measured using a monoclonal antibody (anti-megalin extracellular region monoclonal antibody) against the human megalin extracellular region. The anti-megalin extracellular region monoclonal antibody is a mouse monoclonal antibody that recognizes an epitope that is present in the region (LBD1) between the $26^{th}$ amino acid and the $314^{th}$ amino acid of the amino acid sequence shown in SEQ ID NO: 2. Measurement was evaluated using anti-human megalin LBD1 monoclonal antibody A and anti-human megalin LBD1 monoclonal antibody B recognizing two different epitopes in LBD1. The human megalin extracellular region-containing fragment in urine was measured using a microtiter plate onto which an anti-human megalin LBD1 monoclonal antibody had been immobilized and an ALP-labeled anti-human megalin LBD1 monoclonal antibody B. First, 50 μL of urine and 50 μL of treatment solution A (400 mM Tris-HCl, 40 mM Ethylenediamine-N,N,N',N'-tetraacetic acid (hereinafter, Ethylenediamine-N,N,N',N'-tetraacetic acid is abbreviated as EDTA), 2% (vol./vol.) Polyethylene Glycol Mono-p-isooctylphenyl Ether (hereinafter, Polyethylene Glycol Mono-p-isooctylphenyl Ether is referred to as Triton™ X-100 (octylphenol ethoxylate)), pH 8.0 solution) were mixed. The mixed solution (100 μL) was added to wells of the microtiter plate onto which an anti-human megalin LBD1 monoclonal antibody A had been immobilized (FluoroNunc (Trademark) Module F16 Black-Maxisorp (Trademark) Surface plate, Nalge Nunc International), and then left to stand at 37° C. for 1 hour. Subsequently, the urine sample solution that had been added to wells was removed by decantation. TBS-T was added at 200 μL/well to the wells of the microtiter plate, and then removed by decantation, followed by washing. The washing step was performed 3 times in total. Subsequently, an ALP-labeled anti-human megalin LBD1 monoclonal antibody B (0.5 ng/mL) solution was added at 100 μL/well. The ALP-labeled anti-human megalin LBD1 monoclonal antibody B was prepared with a diluent for a labeled antibody. The resultant was left to stand at 37° C. for 1 hour, and then the ALP-labeled antibody solution that had been added to wells was removed by decantation. TBS-T was added at 200 μL/well to the wells of the microtiter plate, and then removed by decantation, followed by washing. The washing step was performed 4 times in total. Subsequently, an assay buffer was added at 200 μL/well to the wells of the microtiter plate, and then removed by decantation, followed by washing. The washing step was performed 2 times in total. Next, CDP-Star (registered trademark) Chemiluminescent Substrate for Alkaline Phosphatase Ready-to-Use (0.4 mM) with Emerald-II (trademark) Enhancer (ELISA-Light (trademark) System: Applied Biosystems) was added as a substrate solution for ALP enzymatic reaction to wells at 100 μL/well, and then left to stand at 37° C. for 30 minutes while protecting the solution from light. Immediately after the procedure, the cumulative emission intensity of the wells was measured for 1 second. The measured values were used as indicators for evaluation of the measurement of urinary megalin. Microplate Luminometer Centro LB960 and MicroWin2000 software (Berthold) were used for measuring chemiluminescence intensity.

(2) Method for Measuring Urinary Megalin Using Urine Treated with Treatment Solutions Containing Reducing Agents The above treatment solution A containing 1.625 mM glutathione was designated as treatment solution B, the above treatment solution A containing 2 mM cysteine was designated as treatment solution C, and the above treatment solution A containing 2 mM penicillamine was designated as treatment solution D. 50 μL of treatment solution B, C or D and 50 μL of a urine specimen were mixed. Urinary megalin was measured using each mixed solution as a urine sample solution. The measurement method was performed according to Example 1.

(3) Comparison of Assay Sensitivity for Urinary Megalin Between the Presence and the Absence of Reducing Agents Urinary megalin was measured by the methods of (1) and (2) above using urine specimens from two healthy subject cases, and then the measured value of urinary megalin was compared between the presence and the absence of the reducing agents. The results are shown in FIG. 1. In FIG. 1, the vertical axis indicates RLU (Relative Light Unit). As shown in FIG. 1, the assay sensitivity for urinary megalin was increased by the use of the reducing agents. Specifically, the use of the reducing agents makes it possible to increase assay sensitivity, making it possible to measure low-concentration urinary megalin.

Example 2

Examination of the Effective Concentrations of Reducing Agents

The effective concentrations of reducing agents used in Example 1 were examined using 2 healthy subject cases (specimen A and specimen B). The concentrations of the reducing agents, which were examined herein, are as follows: glutathione: 0 mM to 13 mM, cysteine: 0 mM to 16 mM, and penicillamine: 0 mM to 64 mM. The results for glutathione, cysteine and penicillamine are shown in Table 1, Table 2, and Table 3, respectively.

TABLE 1

Table 1 Examination of effective concentrations of glutathione

| Final concentration in urine (mM) | Specimen A | Specimen B |
|---|---|---|
| | RLU | |
| 0.0000 | 4662 | 1569 |
| 0.0127 | 5037 | 1689 |
| 0.0325 | 6435 | 2027 |
| 0.0507 | 9200 | 3974 |
| 0.0650 | 12410 | 3391 |
| 0.0975 | 19913 | 5113 |
| 0.1300 | 28973 | 7799 |
| 0.1625 | 33784 | 9113 |
| 0.1950 | 39771 | 10327 |
| 0.2031 | 70692 | 17162 |
| 0.8125 | 68211 | 15401 |
| 3.2500 | 35390 | 14563 |
| 13.0000 | 6329 | 6138 |

TABLE 2

Table 2 Examination of effective concentrations of cysteine

| Final concentration in urine (mM) | Specimen A | Specimen B |
|---|---|---|
| | RLU | |
| 0 | 4662 | 1569 |
| 0.0625 | 7219 | 2590 |
| 0.0750 | 7533 | 2434 |
| 0.1000 | 11372 | 4121 |
| 0.1250 | 14220 | 6171 |
| 0.1500 | 19778 | 8339 |
| 0.1750 | 29880 | 10088 |
| 0.2000 | 33934 | 9851 |
| 0.2250 | 42210 | 11102 |
| 0.2500 | 85447 | 20045 |
| 1.0000 | 66844 | 16103 |
| 4.0000 | 40183 | 12023 |
| 16.0000 | 10117 | 7002 |

TABLE 3

Table 3 Examination of effective concentrations of penicillamine

| Final concentration in urine (mM) | Specimen A | Specimen B |
|---|---|---|
| | RLU | |
| 0 | 4662 | 1569 |
| 0.0625 | 6710 | 2026 |
| 0.0750 | 7069 | 2442 |
| 0.1000 | 9667 | 3599 |
| 0.1250 | 13138 | 4094 |
| 0.1500 | 16949 | 5029 |
| 0.1750 | 22244 | 6902 |
| 0.2000 | 25704 | 7819 |
| 0.2250 | 32720 | 8321 |
| 0.2500 | 58711 | 16323 |
| 1.0000 | 56122 | 16901 |
| 4.0000 | 46086 | 15100 |
| 16.0000 | 25281 | 10903 |
| 64.0000 | 11352 | 5596 |

The sensitivity for urinary megalin measured using urine subjected to reduction treatment with glutathione having a concentration of 0.0127 mM-13 mM as shown in Table 1, with cysteine having a concentration of 0.0625 mM-16 mM as shown in Table 2, or with penicillamine having a concentration of 0.0625 mM-64 mM as shown in Table 3 was revealed to increase to degrees higher than that for urinary megalin measured using urine not subjected to reduction treatment.

Example 3

Effects of Treatment Solutions Containing Reducing Agents and Chaotropic Reagents in Combination on Assay Sensitivity (1) Measurement of Urinary Megalin Using Urine Treated with Treatment Solutions Containing Reducing Agents and Urea in Combination Treatment solution B of Example 1 (2) containing 640 mM urea in addition to 1.625 mM glutathione as a reducing agent was designated as treatment solution E, treatment solution C of Example 1 (2) containing 640 mM urea in addition to 2 mM cysteine as a reducing agent was designated as treatment solution F, and treatment solution D of Example 1 (2) containing 640 mM urea in addition to 2 mM penicillamine as a reducing agent was designated as treatment solution G. A mixed solution prepared by mixing 50 µL of treatment solution E, F or G and 50 µL of urine was used as a urine sample solution and urinary megalin was measured. The measurement method was performed according to Example 1.

(2) Measurement of Urinary Megalin Using Urine Treated with Treatment Solutions Containing Reducing Agents and Sodium n-Dodecylbenzenesulfonate (SDBS) as a Surfactant in Combination Treatment solution B of Example 1 (2) containing 2.87 mM SDBS in addition to 1.625 mM glutathione as a reducing agent was designated as treatment solution H, treatment solution C of Example 1 (2) containing 2.87 mM SUBS in addition to 2 mM cysteine as a reducing agent was designated as treatment solution I, and treatment solution D of Example 1 (2) containing 2.87 mM SDBS in addition to 2 mM penicillamine as a reducing agent was designated as treatment solution J. A mixed solution prepared by mixing 50 µL of treatment solution H, I or J and 50 µL of urine was used as a urine sample solution and urinary megalin was measured. The measurement method was performed according to Example 1.

(3) Measurement of Urinary Megalin Using Urine Treated with a Treatment Solution Containing a Chaotropic Reagent or a Surfactant Treatment solution A of Example 1 (1) containing 640 mM urea as a chaotropic reagent was designated as treatment solution K, and treatment solution A of Example 1 (1) containing 2.87 mM SUBS as a surfactant was designated as treatment solution L. A mixed solution prepared by mixing 50 µL of treatment solution K or L and 50 µL of a urine specimen was used as a urine sample solution and urinary megalin was measured. The measurement method was performed according to Example 1.

(4) Effects of Treatment Solutions Containing Reducing Agents and Chaotropic Reagents or Surfactants in Combination Urinary megalin was measured by the methods of Example 1 (1) and Example 3 (1)-(3) using a urine specimen from 1 healthy subject case. Thus, the effects of treatment solutions each containing a reducing agent and urea as a chaotropic reagent or SDBS as a surfactant in combination were examined. Table 4, Table 5, Table 6, Table 7, Table 8, and Table 9 show: the effect when a treatment solution containing glutathione and urea in combination was used, the effect when a treatment solution containing cysteine and urea in combination was used, the effect when a treatment solution containing penicillamine and urea in combination was used, the effect when a treatment solution containing glutathione and SDBS in combination was used, the effect when a treatment solution containing cysteine and SDBS in combination was used, and the effect when a treatment solution containing penicillamine and SDBS in combination was used, respectively. As shown in Table 4 to Table 9, assay sensitivity was found to increase to higher degrees by the use of the treatment solution containing both the reducing agent and the chaotropic reagent or the surfactant than that in the case of using the treatment solution containing any one of the reducing agent, the chaotropic reagent, and the surfactant. Specifically, the use of the treatment solution containing both the reducing agent and the chaotropic reagent or the surfactant makes it possible to increase assay sensitivity, making it possible to measure low-concentration urinary megalin.

TABLE 4

Table 4 Examination of the effects of treatment solutions containing glutathione and urea in combination

|  | RLU |
| --- | --- |
| Reducing agent, no urea added | 6354 |
| Urea | 6480 |
| Glutathione | 35594 |
| Glutathione + Urea | 40737 |

TABLE 5

Table 5 Examination of the effects of treatment solutions containing cysteine and urea in combination

|  | RLU |
| --- | --- |
| Reducing agent, no urea added | 6354 |
| Urea | 6480 |
| Cysteine | 35161 |
| Cysteine + Urea | 45544 |

TABLE 6

Table 6 Examination of the effects of treatment solutions containing penicillamine and urea in combination

|  | RLU |
| --- | --- |
| Reducing agent, no urea added | 6354 |
| Urea | 6480 |
| Penicillamine | 35996 |
| Penicillamine + Urea | 52485 |

TABLE 7

Table 7 Examination of the effects of treatment solutions containing glutathione and SDBS in combination

|  | RLU |
| --- | --- |
| Reducing agent and no SDBS added | 6354 |
| SDBS | 7751 |
| Glutathione | 35594 |
| Glutathione + SDBS | 42353 |

TABLE 8

Table 8 Examination of the effects of treatment solutions containing cysteine and SDBS in combination

|  | RLU |
| --- | --- |
| Reducing agent, no SDBS added | 6354 |
| SDBS | 7751 |
| Cysteine | 35161 |
| Cysteine + SDBS | 46735 |

TABLE 9

Table 9 Examination of the effects of treatment solutions containing penicillamine and SDBS in combination

|  | RLU |
| --- | --- |
| Reducing agent, no SDBS added | 6354 |
| SDBS | 7751 |
| Penicillamine | 35996 |
| Penicillamine + SDBS | 50733 |

Example 4

Examination of the Effective Concentration of a Chaotropic Reagent or a Surfactant when a Reducing Agent and the Chaotropic Reagent or the Surfactant were Combined The effective concentration of the chaotropic reagent or the surfactant used in Example 3 (1) and (2) was examined using a urine specimen from one healthy subject case. The concentrations of reducing agents in urine specimens are as follows: the concentration of glutathione was 0.8125 mM, the same of cysteine was 1 mM, and the same of penicillamine was 1 mM. The concentration of urea that is a chaotropic reagent or the same of SDBS that is a surfactant in the urine specimen was as follows: the concentration of urea examined; 0 mM-320 mM and the same of SDBS examined; 0 mM-5.74 mM. The results are shown in Table 10 and Table 11. Assay sensitivity was found to increase to higher degrees when urinary megalin was measured after the treatment of urine with a reducing agent and the chaotropic reagent or the surfactant; that is, the treatment of urine with urea having a concentration of 5 mM-320 mM in the presence of the reducing agents as shown in Table 10 or with SDBS having a concentration of 1.43 mM-5.74 mM in the presence of the reducing agents as shown in Table 11, than that in the case of urinary megalin measurement after the treatment of urine with only the reducing agents.

TABLE 10

Table 10 Examination of the effective concentrations of urea when used in combination with reducing agents

| | Urea + Reducing agent | | |
| --- | --- | --- | --- |
| Urea (mM) | Glutathione | Cysteine | Penicillamine |
| | | RLU | |
| 0 | 35594 | 35161 | 35996 |
| 5 | 36887 | 38541 | 49170 |
| 20 | 38649 | 41687 | 47767 |
| 80 | 38598 | 41936 | 42532 |
| 160 | 39081 | 40313 | 41831 |
| 320 | 40737 | 45544 | 52485 |

TABLE 11

Table 11 Examination of the effective concentrations of SDBS when used in combination with reducing agents

| | SDBS + Reducing agent | | |
| --- | --- | --- | --- |
| SDBS (mM) | Glutathione | Cysteine | Penicillamine |
| | | RLU | |
| 0 | 35594 | 35161 | 35996 |
| 1.43 | 42353 | 46735 | 50733 |
| 5.74 | 40512 | 42916 | 48650 |

All publications, patents, and patent applications cited herein are incorporated herein by reference in their entirety.

The invention claimed is:

1. An immunoassay method for measuring a protein in a urine specimen, comprising pretreating the urine specimen by mixing the urine specimen with cysteine and urea, or cysteine and sodium n-dodecylbenzenesulfonate (SDBS), and then measuring the protein in the urine specimen by performing immunoassay, thereby improving assay sensitivity for the protein.

2. The immunoassay method according to claim 1, comprising pretreating the urine specimen by mixing the urine specimen with 0.0625 mM to 16 mM cysteine and 5 mM to 320 mM urea, or 0625 mM to 16 mM cysteine and 1.43 mM to 5.74 mM sodium n-dodecylbenzenesulfonate (SDBS), and then measuring the protein in the urine specimen by performing immunoassay.

3. The immunoassay method according to claim 1, wherein the protein is megalin.

4. An immunoassay method for measuring a protein in a urine specimen, comprising pretreating the urine specimen by mixing the urine specimen with penicillamine and urea or penicillamine and sodium n-dodecylbenzenesulfonate (SDBS), and then measuring the protein in the urine specimen by performing immunoassay, thereby improving assay sensitivity for the protein.

5. The immunoassay method according to claim 4, comprising pretreating the urine specimen by mixing the urine specimen with 0.0625 mM to 64 mM penicillamine and 5 mM to 320 mM urea, or 0625 mM to 64 mM penicillamine and 1.43 mM to 5.74 mM sodium n-dodecylbenzenesulfonate (SDBS), and then measuring the protein in the urine specimen by performing immunoassay.

6. The immunoassay method according to claim 4, wherein the protein is megalin.

* * * * *

SEQUENCE LISTING

<160> NUMBER OF SEQ ID NOS: 2

<210> SEQ ID NO 1
<211> LENGTH: 13968
<212> TYPE: DNA
<213> ORGANISM: Homo sapiens

<400> SEQUENCE: 1

| | | | | | |
|---|---|---|---|---|---|
| atggatcgcg | ggccggcagc | agtggcgtgc | acgctgctcc | tggctctcgt | cgcctgccta | 60 |
| gcgccggcca | gtggccaaga | atgtgacagt | gcgcattttc | gctgtggaag | tgggcattgc | 120 |
| atccctgcag | actggaggtg | tgatgggacc | aaagactgtt | cagatgacgc | ggatgaaatt | 180 |
| ggctgcgctg | ttgtgacctg | ccagcagggc | tatttcaagt | gccagagtga | gggacaatgc | 240 |
| atccccagct | cctgggtgtg | tgaccaagat | caagactgtg | atgatggctc | agatgaacgt | 300 |
| caagattgct | cacaaagtac | atgctcaagt | catcagataa | catgctccaa | tggtcagtgt | 360 |
| atcccaagtg | aatacaggtg | cgaccacgtc | agagactgcc | ccgatggagc | tgatgagaat | 420 |
| gactgccagt | acccaacatg | tgagcagctt | acttgtgaca | atgggcctg | ctataacacc | 480 |
| agtcagaagt | gtgattggaa | agttgattgc | agggactcct | cagatgaaat | caactgcact | 540 |
| gagatatgct | tgcacaatga | gttttcatgt | ggcaatggag | agtgtatccc | tcgtgcttat | 600 |
| gtctgtgacc | atgacaatga | ttgccaagac | ggcagtgatg | aacatgcttg | caactatccg | 660 |
| acctgcggtg | gttaccagtt | cacttgcccc | agtggccgat | gcatttatca | aaactgggtt | 720 |
| tgtgatggag | aagatgactg | taaagataat | ggagatgaag | atggatgtga | aagcggtcct | 780 |
| catgatgttc | ataaatgttc | cccaagagaa | tggtcttgcc | cagagtcggg | acgatgcatc | 840 |
| tccatttata | agtttgtga | tgggatttta | gattgcccag | aagagaaga | tgaaaacaac | 900 |
| actagtaccg | aaaatactg | tagtatgact | ctgtgctctg | ccttgaactg | ccagtaccag | 960 |
| tgccatgaga | cgccgtatgg | aggagcgtgt | ttttgtcccc | caggttatat | catcaaccac | 1020 |
| aatgacagcc | gtacctgtgt | tgagtttgat | gattgccaga | tatgggaat | ttgtgaccag | 1080 |
| aagtgtgaaa | gccgacctgg | ccgtcacctg | tgccactgtg | aagaagggta | tatcttggag | 1140 |
| cgtggacagt | attgcaaagc | taatgattcc | tttggcgagg | cctccattat | cttctccaat | 1200 |
| ggtcgggatt | tgttaattgg | tgatattcat | ggaaggagct | tccggatcct | agtggagtct | 1260 |
| cagaatcgtg | gagtggccgt | gggtgtggct | ttccactatc | acctgcaaag | agttttttgg | 1320 |
| acagacaccg | tgcaaaataa | ggttttttca | gttgacatta | atggtttaaa | tatccaagag | 1380 |
| gttctcaatg | tttctgttga | aaccccagag | aacctggctg | tggactgggt | taataataaa | 1440 |
| atctatctag | tggaaaccaa | ggtcaaccgc | atagatatgg | taaatttgga | tggaagctat | 1500 |
| cgggttaccc | ttataactga | aaacttgggg | catcctagag | aattgccgt | ggacccaact | 1560 |
| gttggttatt | tattttctc | agattgggag | agccttctg | gggaacctaa | gctgaaagg | 1620 |
| gcattcatgg | atgcagcaa | ccgtaaagac | ttggtgaaaa | caaagctggg | atggcctgct | 1680 |
| ggggtaactc | tggatatgat | atcgaagcgt | gtttactggg | ttgactctcg | gtttgattac | 1740 |
| attgaaactg | taacttatga | tggaattcaa | aggaagactg | tagttcatgg | aggctccctc | 1800 |
| attcctcatc | cctttggagt | aagcttattt | gaaggtcagg | tgttctttac | agattggaca | 1860 |
| aagatggccg | tgctgaaggc | aaacaagttc | acagagacca | accacaagt | gtactaccag | 1920 |
| gcttccctga | ggccctatgg | agtgactgtt | taccattccc | tcagacagcc | ctatgctacc | 1980 |
| aatccgtgta | aagataacaa | tgggggctgt | gagcaggtct | gtgttctcag | ccacagaaca | 2040 |
| gataatgatg | gtttgggttt | ccgttgcaag | tgcacattcg | gcttccaact | ggatacagat | 2100 |

```
gagcgccact gcattgctgt tcagaatttc ctcattttt catcccaagt tgctattcgt    2160
gggatcccgt tcaccttgtc tacccaggaa gatgtcatgg ttccagtttc ggggaatcct    2220
tctttctttg tcgggattga ttttgacgcc caggacagca ctatcttttt ttcagatatg    2280
tcaaaacaca tgatttttaa gcaaaagatt gatggcacag gaagagaaat tctcgcagct    2340
aacagggtgg aaaatgttga aagtttggct tttgattgga tttcaaagaa tctctattgg    2400
acagactctc attacaagag tatcagtgtc atgaggctag ctgataaaac gagacgcaca    2460
gtagttcagt atttaaataa cccacggtcg gtggtagttc atccttttgc cgggtatcta    2520
ttcttcactg attggttccg tcctgctaaa attatgagag catggagtga cggatctcac    2580
ctcttgcctg taataaacac tactcttgga tgcccaatg gcttggccat cgattgggct     2640
gcttcacgat tgtactgggt agatgcctat tttgataaaa ttgagcacag cacctttgat    2700
ggtttagaca gaagaagact gggccatata gagcagatga cacatccgtt tggacttgcc    2760
atctttggag agcatttatt ttttactgac tggagactgg gtgccattat tcgagtcagg    2820
aaagcagatg gtggagaaat gacagttatc cgaagtggca ttgcttacat actgcatttg    2880
aaatcgtatg atgtcaacat ccagactggt tctaacgcct gtaatcaacc cacgcatcct    2940
aacggtgact gcagccactt ctgcttcccg gtgccaaatt tccagcgagt gtgtgggtgc    3000
ccttatggaa tgaggctggc ttccaatcac ttgacatgcg agggggaccc aaccaatgaa    3060
ccacccacgg agcagtgtgg cttattttcc ttcccctgta aaaatggcag atgtgtgccc    3120
aattactatc tctgtgatgg agtcgatgat tgtcatgata acagtgatga gcaactatgt    3180
ggcacactta ataatacctg ttcatcttcg gcgttcacct gtggccatgg ggagtgcatt    3240
cctgcacact ggcgctgtga caaacgcaac gactgtgtgg atggcagtga tgagcacaac    3300
tgccccaccc acgcacctgc ttcctgcctt gacacccaat acacctgtga taatcaccag    3360
tgtatctcaa agaactgggt ctgtgacaca gacaatgatt gtggggatgg atctgatgaa    3420
aagaactgca attcgacaga gacatgccaa cctagtcagt ttaattgccc caatcatcga    3480
tgtattgacc tatcgtttgt ctgtgatggt gacaaggatt gtgttgatgg atctgatgag    3540
gttggttgtg tattaaactg tactgcttct caattcaagt gtgccagtgg ggataaatgt    3600
attggcgtca caaatcgttg tgatggtgtt tttgattgca gtgacaactc ggatgaagcg    3660
ggctgtccaa ccaggcctcc tggtatgtgc cactcagatg aatttcagtg ccaagaagat    3720
ggtatctgca tcccgaactt ctgggaatgt gatgggcatc cagactgcct ctatggatct    3780
gatgagcaca atgcctgtgt ccccaagact tgcccttcat catatttcca ctgtgacaac    3840
ggaaactgca tccacagggc atggctctgt gatcgggaca tgactgcgg ggatatgagt     3900 gatgagaagg actgccctac tcagccctt cgctgtccta gttggcaatg gcagtgtctt     3960
ggccataaca tctgtgtgaa tctgagtgta gtgtgtgatg gcatctttga ctgccccaat    4020
gggacagatg agtccccact ttgcaatggg aacagctgct cagatttcaa tggtggttgt    4080
actcacgagt gtgttcaaga gccctttggg gctaaatgcc tatgtccatt gggattctta    4140
cttgccaatg attctaagac ctgtgaagac atagatgaat gtgatattct aggctcttgt    4200
agccagcact gttacaatat gagaggttct ttccggtgct cgtgtgatac aggctacatg    4260
ttagaaagtg atgggaggac ttgcaaagtt acagcatctg agagtctgct gttacttgtg    4320
gcaagtcaga acaaaattat tgccgacagt gtcacctccc aggtccacaa tatctattca    4380
ttggtcgaga atggttctta cattgtagct gttgattttg attcaattag tggtcgtatc    4440
```

```
ttttggtctg atgcaactca gggtaaaacc tggagtgcgt ttcaaaatgg aacggacaga    4500
agagtggtat ttgacagtag catcatcttg actgaaacta ttgcaataga ttgggtaggt    4560
cgtaatcttt actggacaga ctatgctctg gaaacaattg aagtctccaa aattgatggg    4620
agccacagga ctgtgctgat tagtaaaaac ctaacaaatc caagaggact agcattagat    4680
cccagaatga atgagcatct actgttctgg tctgactggg gccaccaccc tcgcatcgag    4740
cgagccagca tggacggcag catgcgcact gtcattgtcc aggacaagat cttctggccc    4800
tgcggcttaa ctattgacta ccccaacaga ctgctctact tcatggactc ctatcttgat    4860
tacatggact tttgcgatta taatggacac catcggagac aggtgatagc cagtgatttg    4920
attatacggc accccctatgc cctaactctc tttgaagact ctgtgtactg gactgaccgt    4980
gctactcgtc gggttatgcg agccaacaag tggcatggag ggaaccagtc agttgtaatg    5040
tataatattc aatggcccct tgggattgtt gcggttcatc cttcgaaaca accaaattcc    5100
gtgaatccat gtgccttttc ccgctgcagc catctctgcc tgctttcctc acaggggcct    5160 cattttact cctgtgtttg tccttcagga tggagtctgt ctcctgatct cctgaattgc    5220
ttgagagatg atcaaccttt cttaataact gtaaggcaac atataatttt tggaatctcc    5280
cttaatcctg aggtgaagag caatgatgct atggtcccca tagcagggat acagaatggt    5340
ttagatgttg aatttgatga tgctgagcaa tacatctatt gggttgaaaa tccaggtgaa    5400
attcacagag tgaagacaga tggcaccaac aggacagtat ttgcttctat atctatggtg    5460
gggccttcta tgaacctggc cttagattgg atttcaagaa acctttattc taccaatcct    5520
agaactcagt caatcgaggt tttgacactc acggagata tcagatacag aaaaacattg    5580
attgccaatg atgggacagc tcttggagtt ggctttccaa ttggcataac tgttgatcct    5640
gctcgtggga agctgtactg gtcagaccaa ggaactgaca gtggggttcc tgccaagatc    5700
gccagtgcta acatggatgg cacatctgtg aaaactctct ttactgggaa cctcgaacac    5760
ctggagtgtg tcactcttga catcgaagag cagaaactct actgggcagt cactggaaga    5820
ggagtgattg aaagaggaaa cgtggatgga acagatcgga tgatcctggt acaccagctt    5880
tcccacccct ggggaattgc agtccatgat tcttttcctt attatactga tgaacagtat    5940
gaggtcattg aaagagttga taaggccact ggggccaaca aaatagtctt gagagataat    6000
gttccaaatc tgagggtct tcaagtttat cacagacgca atgccgccga atcctcaaat    6060
ggctgtagca acaacatgaa tgcctgtcag cagatttgcc tgcctgtacc aggaggattg    6120
ttttcctgcg cctgtgccac tggatttaaa ctcaatcctg ataatcggtc ctgctctcca    6180
tataactctt tcattgttgt ttcaatgctg tctgcaatca gaggctttag cttggaattg    6240
tcagatcatt cagaaaccat ggtgccggtg gcaggccaag gacgaaacgc actgcatgtg    6300
gatgtggatg tgtcctctgg ctttatttat tggtgtgatt ttagcagctc agtggcatct    6360
gataatgcga tccgtagaat taaaccagat ggatcttctc tgatgaacat tgtgacacat    6420
ggaataggag aaaatggagt ccggggtatt gcagtggatt gggtagcagg aaatctttat    6480
ttcaccaatg cctttgtttc tgaaacactg atagaagttc tgcggatcaa tactacttac    6540
cgccgtgttc ttcttaaagt cacagtggac atgcctaggc atattgttgt agatcccaag    6600
aacagatacc tcttctgggc tgactatggg cagagaccaa agattgagcg ttctttcctt    6660
gactgtacca atcgaacagt gcttgtgtca gagggcattg tcacaccacg gggcttggca    6720
gtggaccgaa gtgatggcta cgtttattgg gttgatgatt ctttagatat aattgcaagg    6780
attcgtatca atggagagaa ctctgaagtg attcgttatg gcagtcgtta cccaactcct    6840
```

```
tatggcatca ctgtttttga aaattctatc atatgggtag ataggaattt gaaaaagatc    6900
ttccaagcca gcaaggaacc agagaacaca gagccaccca cagtgataag agacaatatc    6960
aactggctaa gagatgtgac catctttgac aagcaagtcc agccccggtc accagcagag    7020
gtcaacaaca acccttgctt ggaaaacaat ggtgggtgct ctcatctctg ctttgctctg    7080
cctggattgc acaccccaaa atgtgactgt gcctttggga ccctgcaaag tgatggcaag    7140
aattgtgcca tttcaacaga aaatttcctc atctttgcct tgtctaattc cttgagaagc    7200
ttacacttgg accctgaaaa ccatagccca cctttccaaa caataaatgt ggaaagaact    7260
gtcatgtctc tagactatga cagtgtaagt gatagaatct acttcacaca aaatttagcc    7320
tctggagttg gacagatttc ctatgccacc ctgtcttcag ggatccatac tccaactgtc    7380
attgcttcag gtatagggac tgctgatggc attgcctttg actggattac tagaagaatt    7440
tattacagtg actacctcaa ccagatgatt aattccatgg ctgaagatgg gtctaaccgc    7500
actgtgatag cccgcgttcc aaaaccaaga gcaattgtgt tagatccctg ccaagggtac    7560
ctgtactggg ctgactggga tacacatgcc aaaatcgaga gagccacatt gggaggaaac    7620
ttccgggtac ccattgtgaa cagcagtctg gtcatgccca gtgggctgac tctggactat    7680
gaagaggacc ttctctactg ggtggatgct agtctgcaga ggattgaacg cagcactctg    7740
acgggcgtgg atcgtgaagt cattgtcaat gcagccgttc atgcttttgg cttgactctc    7800
tatggccagt atatttactg gactgacttg tacacacaaa gaatttaccg agctaacaaa    7860
tatgacgggg caggtcagat tgcaatgacc acaaatttgc tctcccagcc caggggaatc    7920
aacactgttg tgaagaacca gaaacaacag tgtaacaatc cttgtgaaca gtttaatggg    7980
ggctgcagcc atatctgtgc accaggtcca aatggtgccg agtgccagtg tccacatgag    8040
ggcaactggt atttggccaa caacaggaag cactgcattg tggacaatgg tgaacgatgt    8100
ggtgcatctt ccttcacctg ctccaatggg cgctgcatct cggaagagtg gaagtgtgat    8160
aatgacaacg actgtgggga tggcagtgat gagatggaaa gtgtctgtgc acttcacacc    8220
tgctcaccga cagccttcac ctgtgccaat gggcgatgtg tccaatactc ttaccgctgt    8280
gattactaca atgactgtgg tgatggcagt gatgaggcag ggtgcctgtt cagggactgc    8340
aatgccacca cggagtttat gtgcaataac agaaggtgca tacctcgtga gtttatctgc    8400
aatggtgtag acaactgcca tgataataac acttcagatg agaaaaattg ccctgatcgc    8460
acttgccagt ctggatacac aaaatgtcat aattcaaata tttgtattcc tcgcgtttat    8520
ttgtgtgacg gagacaatga ctgtggagat aacagtgatg aaaaccctac ttattgcacc    8580
actcacacat gcagcagcag tgagttccaa tgcgcatctg ggcgctgtat tcctcaacat    8640
tggtattgtg atcaagaaac agattgtttt gatgcctctg atgaacctgc tcttgtggt     8700 cactctgagc gaacatgcct agctgatgag ttcaagtgtg atggtgggag gtgcatccca    8760
agcgaatgga tctgtgacgg tgataatgac tgtgggggata tgagtgacga ggataaaagg    8820
caccagtgtc agaatcaaaa ctgctcggat tccgagtttc tctgtgtaaa tgacagacct    8880
ccggacagga ggtgcattcc ccagtcttgg gtctgtgatg gcgatgtgga ttgtactgac    8940
ggctacgatg agaatcagaa ttgcaccagg agaacttgct ctgaaaatga attcacctgt    9000
ggttacggac tgtgtatccc aaagatattc aggtgtgacc ggcacaatga ctgtggtgac    9060
tatagcgacg agaggggctg cttataccag acttgccaac agaatcagtt tacctgtcag    9120
aacgggcgct gcattagtaa aaccttcgtc tgtgatgagg ataatgactg tggagacgga    9180
```

```
tctgatgagc tgatgcacct gtgccacacc ccagaaccca cgtgtccacc tcacgagttc   9240
aagtgtgaca atgggcgctg catcgagatg atgaaactct gcaaccacct agatgactgt   9300
ttggacaaca gcgatgagaa aggctgtggc attaatgaat gccatgaccc ttcaatcagt   9360
ggctgcgatc acaactgcac agacaccta accagtttct attgttcctg tcgtcctggt    9420
tacaagctca tgtctgacaa gcggacttgt gttgatattg atgaatgcac agagatgcct   9480
tttgtctgta gccagaagtg tgagaatgta ataggctcct acatctgtaa gtgtgcccca   9540
ggctacctcc gagaaccaga tggaaagacc tgccggcaaa acagtaacat cgaaccctat   9600
ctcattttta gcaaccgtta ctatttgaga aatttaacta tagatggcta tttttactcc   9660
ctcatcttgg aaggactgga caatgttgtg gcattagatt ttgaccgagt agagaagaga   9720
ttgtattgga ttgatacaca gaggcaagtc attgagagaa tgtttctgaa taagacaaac   9780
aaggagacaa tcataaacca cagactacca gctgcagaaa gtctggctgt agactgggtt   9840
tccagaaagc tctactggtt ggatgcccgc ctggatggcc tctttgtctc tgacctcaat   9900
ggtgacacc gccgcatgct ggcccagcac tgtgtggatg ccaacaacac cttctgcttt    9960
gataatccca gaggacttgc ccttcaccct caatatgggt acctctactg gcagactgg   10020
ggtcaccgcg catacattgg gagagtaggc atggatggaa ccaacaagtc tgtgataatc   10080
tccaccaagt tagagtggcc taatggcatc accattgatt acaccaatga tctactctac   10140
tgggcagatg cccacctggg ttacatagag tactctgatt tggagggcca ccatcgacac   10200
acggtgtatg atggggcact gcctcacccc tttcgctatta ccattttga agacactatt   10260
tattggacag attggaatac aaggacagtg gaaaagggaa acaaatatga tggatcaaat   10320
agacagacac tggtgaacac aacacacaga ccattgaca tccatgtgta ccatccatat   10380
aggcagccca ttgtgagcaa tccctgtggt accaacaatg gtggctgttc tcatctctgc   10440
ctcatcaagc caggaggaaa agggtcact tgcgagtgtc cagatgactt ccgcacccctt   10500
caactgagtg gcagcaccta ctgcatgccc atgtgctcca gcacccagtt cctgtgcgct   10560
aacaatgaaa agtgcattcc tatctggtgg aaatgtgatg acagaaaga ctgctcagat   10620
ggctctgatg aactggccct ttgccgcag cgcttctgcc gactgggaca gttccagtgc   10680
agtgacggca actgcaccag cccgcagact ttatgcaatg ctcaccaaaa ttgccctgat   10740
gggtctgatg aagaccgtct tctttgtgag aatcaccact gtgactccaa tgaatggcag   10800
tgcgccaaca acgttgcat cccagaatcc tggcagtgtg acacatttaa cgactgtgag    10860
gataactcag atgaagacag ttcccactgt gccagcagga cctgccggcc gggccagttt   10920
cggtgtgcta atggccgctg catcccgcag gcctggaagt gtgatgtgga taatgattgt   10980
ggagaccact cggatgagcc cattgaagaa tgcatgagct ctgccatct ctgtgacaac   11040
ttcacagaat tcagctgcaa aacaaattac cgctgcatcc caaagtgggc cgtgtgcaat   11100
ggtgtagatg actgcaggga caacagtgat gagcaaggct gtgaggagag acatgccat   11160
cctgtggggg atttccgctg taaaaatcac cactgcatcc ctcttcgttg gcagtgtgat   11220
gggcaaaatg actgtggaga taactcagat gaggaaaact gtgctccccg ggagtgcaca   11280
gagagcgagt tcgatgtgt caatcagcag tgcattccct cgcgatggat ctgtgaccat   11340
tacaacgact gtgggacaa ctcagatgaa cgggactgtg agatgaggac ctgccatcct   11400
gaatatttc agtgtacaag tggacattgt gtacacagtg aactgaaatg cgatggatcc   11460
gctgactgtt ggatgcgtc tgatgaagct gattgtccca cacgctttcc tgatggtgca   11520
tactgccagg ctactatgtt cgaatgcaaa aaccatgttt gtatcccgcc atattggaaa   11580
```

```
tgtgatggcg atgatgactg tggcgatggt tcagatgaag aacttcacct gtgcttggat    11640
gttccctgta attcaccaaa ccgtttccgg tgtgacaaca atcgctgcat ttatagtcat    11700
gaggtgtgca atggtgtgga tgactgtgga gatggaactg atgagacaga ggagcactgt    11760
agaaaaccga cccctaaacc ttgtacagaa tatgaatata agtgtggcaa tgggcattgc    11820
attccacatg acaatgtgtg tgatgatgcc gatgactgtg gtgactggtc cgatgaactg    11880
ggttgcaata aaggaaaaga aagaacatgt gctgaaaata tatgcgagca aaattgtacc    11940
caattaaatg aaggaggatt tatctgctcc tgtacagctg ggttcgaaac caatgttttt    12000
gacagaacct cctgtctaga tatcaatgaa tgtgaacaat ttgggacttg tccccagcac    12060
tgcagaaata ccaaaggaag ttatgagtgt gtctgtgctg atggcttcac gtctatgagt    12120
gaccgccctg gaaaacgatg tgcagctgag ggtagctctc ctttgttgct actgcctgac    12180
aatgtccgaa ttcgaaaata taatctctca tctgagaggt tctcagagta tcttcaagat    12240
gaggaatata tccaagctgt tgattatgat tgggatccca aggacatagg cctcagtgtt    12300
gtgtattaca ctgtgcgagg ggagggctct aggtttggtg ctatcaaacg tgcctacatc    12360
cccaactttg aatccggccg caataatctt gtgcaggaag ttgacctgaa actgaaatac    12420
gtaatgcagc cagatggaat agcagtggac tgggttggaa ggcatattta ctggtcagat    12480
gtcaagaata aacgcattga ggtggctaaa cttgatggaa ggtacagaaa gtggctgatt    12540
tccactgacc tggaccaacc agctgctatt gctgtgaatc ccaaactagg gcttatgttc    12600
tggactgact ggggaaagga acctaaaatc gagtctgcct ggatgaatgg agaggaccgc    12660
aacatcctgg ttttcgagga ccttggttgg ccaactggcc tttctatcga ttatttgaac    12720
aatgaccgaa tctactggag tgacttcaag gaggacgtta ttgaaaccat aaaatatgat    12780
gggactgata ggagagtcat tgcaaaggaa gcaatgaacc cttacagcct ggacatcttt    12840
gaagaccagt tatactggat atctaaggaa aagggagaag tatggaaaca aaataaattt    12900
gggcaaggaa agaaagagaa aacgctggta gtgaacccct tggctcactca agttcgaatc    12960 tttcatcaac tcagatacaa taagtcagtg cccaaccttt gcaaacagat ctgcagccac    13020
ctctgccttc tgagacctgg aggatacagc tgtgcctgtc cccaaggctc cagctttata    13080
gaggggagca ccactgagtg tgatgcagcc atcgaactgc ctatcaacct gccccccccca    13140 tgcaggtgca tgcacggagg aaattgctat tttgatgaga ctgacctccc caaatgcaag    13200
tgtcctagcg gctacaccgg aaaatattgt gaaatggcgt tttcaaaagg catctctcca    13260
ggaacaaccg cagtagctgt gctgttgaca atcctcttga tcgtcgtaat tggagctctg    13320
gcaattgcag gattcttcca ctatagaagg accggctccc ttttgcctgc tctgcccaag    13380
ctgccaagct taagcagtct cgtcaagccc tctgaaaatg ggaatggggt gaccttcaga    13440
tcaggggcag atcttaacat ggatattgga gtgtctggtt ttggacctga gactgctatt    13500
gacaggtcaa tggcaatgag tgaagacttt gtcatggaaa tggggaagca gcccataata    13560
tttgaaaacc caatgtactc agccagagac agtgctgtca aagtggttca gccaatccag    13620
gtgactgtat ctgaaaatgt ggataataag aattatggaa gtcccataaa cccttctgag    13680
atagttccag agacaaaccc aacttccacca gctgctgatg gaactcaggt gacaaaatgg    13740
aatctcttca acgaaaatc taaacaaact accaactttg aaaatccaat ctatgcacag    13800
atggagaacg agcaaaagga aagtgttgct gcgacaccac ctccatcacc ttcgctcccct    13860 gctaagccta agcctccttc gagaagagac ccaactccaa cctattctgc aacagaagac    13920
```

-continued accttttaaag acaccgcaaa tcttgttaaa gaagactctg aagtatag 13968

<210> SEQ ID NO 2
<211> LENGTH: 4655
<212> TYPE: PRT
<213> ORGANISM: Homo sapiens

<400> SEQUENCE: 2

```
Met Asp Arg Gly Pro Ala Ala Val Ala Cys Thr Leu Leu Ala Leu
  1               5                  10                  15

Val Ala Cys Leu Ala Pro Ala Ser Gly Gln Glu Cys Asp Ser Ala His
                 20                  25                  30

Phe Arg Cys Gly Ser Gly His Cys Ile Pro Ala Asp Trp Arg Cys Asp
         35                  40                  45

Gly Thr Lys Asp Cys Ser Asp Asp Ala Asp Glu Ile Gly Cys Ala Val
     50                  55                  60

Val Thr Cys Gln Gln Gly Tyr Phe Lys Cys Gln Ser Glu Gly Gln Cys
 65                  70                  75                  80

Ile Pro Ser Ser Trp Val Cys Asp Gln Asp Gln Asp Cys Asp Asp Gly
                 85                  90                  95

Ser Asp Glu Arg Gln Asp Cys Ser Gln Ser Thr Cys Ser Ser His Gln
                100                 105                 110

Ile Thr Cys Ser Asn Gly Gln Cys Ile Pro Ser Glu Tyr Arg Cys Asp
             115                 120                 125

His Val Arg Asp Cys Pro Asp Gly Ala Asp Glu Asn Asp Cys Gln Tyr
         130                 135                 140

Pro Thr Cys Glu Gln Leu Thr Cys Asp Asn Gly Ala Cys Tyr Asn Thr
145                 150                 155                 160

Ser Gln Lys Cys Asp Trp Lys Val Asp Cys Arg Asp Ser Ser Asp Glu
                165                 170                 175

Ile Asn Cys Thr Glu Ile Cys Leu His Asn Glu Phe Ser Cys Gly Asn
            180                 185                 190

Gly Glu Cys Ile Pro Arg Ala Tyr Val Cys Asp His Asp Asn Asp Cys
        195                 200                 205

Gln Asp Gly Ser Asp Glu His Ala Cys Asn Tyr Pro Thr Cys Gly Gly
    210                 215                 220

Tyr Gln Phe Thr Cys Pro Ser Gly Arg Cys Ile Tyr Gln Asn Trp Val
225                 230                 235                 240

Cys Asp Gly Glu Asp Asp Cys Lys Asp Asn Gly Asp Glu Asp Gly Cys
                245                 250                 255

Glu Ser Gly Pro His Asp Val His Lys Cys Ser Pro Arg Glu Trp Ser
                260                 265                 270

Cys Pro Glu Ser Gly Arg Cys Ile Ser Ile Tyr Lys Val Cys Asp Gly
            275                 280                 285

Ile Leu Asp Cys Pro Gly Arg Glu Asp Glu Asn Asn Thr Ser Thr Gly
        290                 295                 300

Lys Tyr Cys Ser Met Thr Leu Cys Ser Ala Leu Asn Cys Gln Tyr Gln
305                 310                 315                 320

Cys His Glu Thr Pro Tyr Gly Gly Ala Cys Phe Cys Pro Pro Gly Tyr
                325                 330                 335

Ile Ile Asn His Asn Asp Ser Arg Thr Cys Val Glu Phe Asp Asp Cys
                340                 345                 350

Gln Ile Trp Gly Ile Cys Asp Gln Lys Cys Glu Ser Arg Pro Gly Arg
            355                 360                 365
```

-continued

His Leu Cys His Cys Glu Glu Gly Tyr Ile Leu Glu Arg Gly Gln Tyr
370                 375                 380

Cys Lys Ala Asn Asp Ser Phe Gly Glu Ala Ser Ile Ile Phe Ser Asn
385                 390                 395                 400

Gly Arg Asp Leu Leu Ile Gly Asp Ile His Gly Arg Ser Phe Arg Ile
            405                 410                 415

Leu Val Glu Ser Gln Asn Arg Gly Val Ala Val Gly Val Ala Phe His
        420                 425                 430

Tyr His Leu Gln Arg Val Phe Trp Thr Asp Thr Val Gln Asn Lys Val
            435                 440                 445

Phe Ser Val Asp Ile Asn Gly Leu Asn Ile Gln Glu Val Leu Asn Val
450                 455                 460

Ser Val Glu Thr Pro Glu Asn Leu Ala Val Asp Trp Val Asn Asn Lys
465                 470                 475                 480

Ile Tyr Leu Val Glu Thr Lys Val Asn Arg Ile Asp Met Val Asn Leu
                485                 490                 495

Asp Gly Ser Tyr Arg Val Thr Leu Ile Thr Glu Asn Leu Gly His Pro
            500                 505                 510

Arg Gly Ile Ala Val Asp Pro Thr Val Gly Tyr Leu Phe Phe Ser Asp
        515                 520                 525

Trp Glu Ser Leu Ser Gly Glu Pro Lys Leu Glu Arg Ala Phe Met Asp
530                 535                 540

Gly Ser Asn Arg Lys Asp Leu Val Lys Thr Lys Leu Gly Trp Pro Ala
545                 550                 555                 560

Gly Val Thr Leu Asp Met Ile Ser Lys Arg Val Tyr Trp Val Asp Ser
                565                 570                 575

Arg Phe Asp Tyr Ile Glu Thr Val Thr Tyr Asp Gly Ile Gln Arg Lys
            580                 585                 590

Thr Val Val His Gly Gly Ser Leu Ile Pro His Pro Phe Gly Val Ser
        595                 600                 605

Leu Phe Glu Gly Gln Val Phe Phe Thr Asp Trp Thr Lys Met Ala Val
610                 615                 620

Leu Lys Ala Asn Lys Phe Thr Glu Thr Asn Pro Gln Val Tyr Tyr Gln
625                 630                 635                 640

Ala Ser Leu Arg Pro Tyr Gly Val Thr Val Tyr His Ser Leu Arg Gln
                645                 650                 655

Pro Tyr Ala Thr Asn Pro Cys Lys Asp Asn Asn Gly Gly Cys Glu Gln
            660                 665                 670

Val Cys Val Leu Ser His Arg Thr Asp Asn Asp Gly Leu Gly Phe Arg
        675                 680                 685

Cys Lys Cys Thr Phe Gly Phe Gln Leu Asp Thr Asp Glu Arg His Cys
690                 695                 700

Ile Ala Val Gln Asn Phe Leu Ile Phe Ser Ser Gln Val Ala Ile Arg
705                 710                 715                 720

Gly Ile Pro Phe Thr Leu Ser Thr Gln Glu Asp Val Met Val Pro Val
                725                 730                 735

Ser Gly Asn Pro Ser Phe Phe Val Gly Ile Asp Phe Asp Ala Gln Asp
            740                 745                 750

Ser Thr Ile Phe Phe Ser Asp Met Ser Lys His Met Ile Phe Lys Gln
        755                 760                 765

Lys Ile Asp Gly Thr Gly Arg Glu Ile Leu Ala Ala Asn Arg Val Glu
770                 775                 780

Asn Val Glu Ser Leu Ala Phe Asp Trp Ile Ser Lys Asn Leu Tyr Trp

-continued

```
            785                 790                 795                 800
        Thr Asp Ser His Tyr Lys Ser Ile Ser Val Met Arg Leu Ala Asp Lys
                        805                 810                 815
        Thr Arg Arg Thr Val Val Gln Tyr Leu Asn Asn Pro Arg Ser Val Val
                        820                 825                 830
        Val His Pro Phe Ala Gly Tyr Leu Phe Thr Asp Trp Phe Arg Pro
                        835                 840                 845
        Ala Lys Ile Met Arg Ala Trp Ser Asp Gly Ser His Leu Leu Pro Val
                        850                 855                 860
        Ile Asn Thr Thr Leu Gly Trp Pro Asn Gly Leu Ala Ile Asp Trp Ala
        865                 870                 875                 880
        Ala Ser Arg Leu Tyr Trp Val Asp Ala Tyr Phe Asp Lys Ile Glu His
                        885                 890                 895
        Ser Thr Phe Asp Gly Leu Asp Arg Arg Leu Gly His Ile Glu Gln
                        900                 905                 910
        Met Thr His Pro Phe Gly Leu Ala Ile Phe Gly Glu His Leu Phe Phe
                        915                 920                 925
        Thr Asp Trp Arg Leu Gly Ala Ile Ile Arg Val Arg Lys Ala Asp Gly
                        930                 935                 940
        Gly Glu Met Thr Val Ile Arg Ser Gly Ile Ala Tyr Ile Leu His Leu
        945                 950                 955                 960
        Lys Ser Tyr Asp Val Asn Ile Gln Thr Gly Ser Asn Ala Cys Asn Gln
                        965                 970                 975
        Pro Thr His Pro Asn Gly Asp Cys Ser His Phe Cys Phe Pro Val Pro
                        980                 985                 990
        Asn Phe Gln Arg Val Cys Gly Cys Pro Tyr Gly Met Arg Leu Ala Ser
                        995                 1000                1005
        Asn His Leu Thr Cys Glu Gly Asp Pro Thr Asn Glu Pro Pro Thr Glu
                        1010                1015                1020
        Gln Cys Gly Leu Phe Ser Phe Pro Cys Lys Asn Gly Arg Cys Val Pro
        1025                1030                1035                1040
        Asn Tyr Tyr Leu Cys Asp Gly Val Asp Asp Cys His Asp Asn Ser Asp
                        1045                1050                1055
        Glu Gln Leu Cys Gly Thr Leu Asn Asn Thr Cys Ser Ser Ser Ala Phe
                        1060                1065                1070
        Thr Cys Gly His Gly Glu Cys Ile Pro Ala His Trp Arg Cys Asp Lys
                        1075                1080                1085
        Arg Asn Asp Cys Val Asp Gly Ser Asp Glu His Asn Cys Pro Thr His
                        1090                1095                1100
        Ala Pro Ala Ser Cys Leu Asp Thr Gln Tyr Thr Cys Asp Asn His Gln
        1105                1110                1115                1120
        Cys Ile Ser Lys Asn Trp Val Cys Asp Thr Asp Asn Asp Cys Gly Asp
                        1125                1130                1135
        Gly Ser Asp Glu Lys Asn Cys Asn Ser Thr Glu Thr Cys Gln Pro Ser
                        1140                1145                1150
        Gln Phe Asn Cys Pro Asn His Arg Cys Ile Asp Leu Ser Phe Val Cys
                        1155                1160                1165
        Asp Gly Asp Lys Asp Cys Val Asp Gly Ser Asp Glu Val Gly Cys Val
                        1170                1175                1180
        Leu Asn Cys Thr Ala Ser Gln Phe Lys Cys Ala Ser Gly Asp Lys Cys
        1185                1190                1195                1200
        Ile Gly Val Thr Asn Arg Cys Asp Gly Val Phe Asp Cys Ser Asp Asn
                        1205                1210                1215
```

-continued

```
Ser Asp Glu Ala Gly Cys Pro Thr Arg Pro Pro Gly Met Cys His Ser
        1220                1225                1230

Asp Glu Phe Gln Cys Gln Glu Asp Gly Ile Cys Ile Pro Asn Phe Trp
        1235                1240                1245

Glu Cys Asp Gly His Pro Asp Cys Leu Tyr Gly Ser Asp Glu His Asn
        1250                1255                1260

Ala Cys Val Pro Lys Thr Cys Pro Ser Ser Tyr Phe His Cys Asp Asn
1265                1270                1275                1280

Gly Asn Cys Ile His Arg Ala Trp Leu Cys Asp Arg Asp Asn Asp Cys
            1285                1290                1295

Gly Asp Met Ser Asp Glu Lys Asp Cys Pro Thr Gln Pro Phe Arg Cys
            1300                1305                1310

Pro Ser Trp Gln Trp Gln Cys Leu Gly His Asn Ile Cys Val Asn Leu
        1315                1320                1325

Ser Val Val Cys Asp Gly Ile Phe Asp Cys Pro Asn Gly Thr Asp Glu
        1330                1335                1340

Ser Pro Leu Cys Asn Gly Asn Ser Cys Ser Asp Phe Asn Gly Gly Cys
1345                1350                1355                1360

Thr His Glu Cys Val Gln Glu Pro Phe Gly Ala Lys Cys Leu Cys Pro
            1365                1370                1375

Leu Gly Phe Leu Leu Ala Asn Asp Ser Lys Thr Cys Glu Asp Ile Asp
            1380                1385                1390

Glu Cys Asp Ile Leu Gly Ser Cys Ser Gln His Cys Tyr Asn Met Arg
        1395                1400                1405

Gly Ser Phe Arg Cys Ser Cys Asp Thr Gly Tyr Met Leu Glu Ser Asp
        1410                1415                1420

Gly Arg Thr Cys Lys Val Thr Ala Ser Glu Ser Leu Leu Leu Leu Val
1425                1430                1435                1440

Ala Ser Gln Asn Lys Ile Ile Ala Asp Ser Val Thr Ser Gln Val His
            1445                1450                1455

Asn Ile Tyr Ser Leu Val Glu Asn Gly Ser Tyr Ile Val Ala Val Asp
            1460                1465                1470

Phe Asp Ser Ile Ser Gly Arg Ile Phe Trp Ser Asp Ala Thr Gln Gly
        1475                1480                1485

Lys Thr Trp Ser Ala Phe Gln Asn Gly Thr Asp Arg Arg Val Val Phe
        1490                1495                1500

Asp Ser Ser Ile Ile Leu Thr Glu Thr Ile Ala Ile Asp Trp Val Gly
1505                1510                1515                1520

Arg Asn Leu Tyr Trp Thr Asp Tyr Ala Leu Glu Thr Ile Glu Val Ser
            1525                1530                1535

Lys Ile Asp Gly Ser His Arg Thr Val Leu Ile Ser Lys Asn Leu Thr
            1540                1545                1550

Asn Pro Arg Gly Leu Ala Leu Asp Pro Arg Met Asn Glu His Leu Leu
        1555                1560                1565

Phe Trp Ser Asp Trp Gly His Pro Arg Ile Glu Arg Ala Ser Met
        1570                1575                1580

Asp Gly Ser Met Arg Thr Val Ile Val Gln Asp Lys Ile Phe Trp Pro
1585                1590                1595                1600

Cys Gly Leu Thr Ile Asp Tyr Pro Asn Arg Leu Leu Tyr Phe Met Asp
            1605                1610                1615

Ser Tyr Leu Asp Tyr Met Asp Phe Cys Asp Tyr Asn Gly His His Arg
            1620                1625                1630
```

Arg Gln Val Ile Ala Ser Asp Leu Ile Ile Arg His Pro Tyr Ala Leu
            1635                1640                1645

Thr Leu Phe Glu Asp Ser Val Tyr Trp Thr Asp Arg Ala Thr Arg Arg
    1650                1655                1660

Val Met Arg Ala Asn Lys Trp His Gly Gly Asn Gln Ser Val Val Met
1665                1670                1675                1680

Tyr Asn Ile Gln Trp Pro Leu Gly Ile Val Ala Val His Pro Ser Lys
                1685                1690                1695

Gln Pro Asn Ser Val Asn Pro Cys Ala Phe Ser Arg Cys Ser His Leu
            1700                1705                1710

Cys Leu Leu Ser Ser Gln Gly Pro His Phe Tyr Ser Cys Val Cys Pro
        1715                1720                1725

Ser Gly Trp Ser Leu Ser Pro Asp Leu Leu Asn Cys Leu Arg Asp Asp
    1730                1735                1740

Gln Pro Phe Leu Ile Thr Val Arg Gln His Ile Ile Phe Gly Ile Ser
1745                1750                1755                1760

Leu Asn Pro Glu Val Lys Ser Asn Asp Ala Met Val Pro Ile Ala Gly
            1765                1770                1775

Ile Gln Asn Gly Leu Asp Val Glu Phe Asp Asp Ala Glu Gln Tyr Ile
            1780                1785                1790

Tyr Trp Val Glu Asn Pro Gly Glu Ile His Arg Val Lys Thr Asp Gly
        1795                1800                1805

Thr Asn Arg Thr Val Phe Ala Ser Ile Ser Met Val Gly Pro Ser Met
    1810                1815                1820

Asn Leu Ala Leu Asp Trp Ile Ser Arg Asn Leu Tyr Ser Thr Asn Pro
1825                1830                1835                1840

Arg Thr Gln Ser Ile Glu Val Leu Thr Leu His Gly Asp Ile Arg Tyr
            1845                1850                1855

Arg Lys Thr Leu Ile Ala Asn Asp Gly Thr Ala Leu Gly Val Gly Phe
            1860                1865                1870

Pro Ile Gly Ile Thr Val Asp Pro Ala Arg Gly Lys Leu Tyr Trp Ser
        1875                1880                1885

Asp Gln Gly Thr Asp Ser Gly Val Pro Ala Lys Ile Ala Ser Ala Asn
    1890                1895                1900

Met Asp Gly Thr Ser Val Lys Thr Leu Phe Thr Gly Asn Leu Glu His
1905                1910                1915                1920

Leu Glu Cys Val Thr Leu Asp Ile Glu Glu Gln Lys Leu Tyr Trp Ala
            1925                1930                1935

Val Thr Gly Arg Gly Val Ile Glu Arg Gly Asn Val Asp Gly Thr Asp
            1940                1945                1950

Arg Met Ile Leu Val His Gln Leu Ser His Pro Trp Gly Ile Ala Val
        1955                1960                1965

His Asp Ser Phe Leu Tyr Tyr Thr Asp Glu Gln Tyr Glu Val Ile Glu
    1970                1975                1980

Arg Val Asp Lys Ala Thr Gly Ala Asn Lys Ile Val Leu Arg Asp Asn
1985                1990                1995                2000

Val Pro Asn Leu Arg Gly Leu Gln Val Tyr His Arg Arg Asn Ala Ala
            2005                2010                2015

Glu Ser Ser Asn Gly Cys Ser Asn Asn Met Asn Ala Cys Gln Gln Ile
            2020                2025                2030

Cys Leu Pro Val Pro Gly Gly Leu Phe Ser Cys Ala Cys Ala Thr Gly
        2035                2040                2045

Phe Lys Leu Asn Pro Asp Asn Arg Ser Cys Ser Pro Tyr Asn Ser Phe

```
                    2050                2055                2060
Ile Val Val Ser Met Leu Ser Ala Ile Arg Gly Phe Ser Leu Glu Leu
2065                2070                2075                2080

Ser Asp His Ser Glu Thr Met Val Pro Val Ala Gly Gln Gly Arg Asn
            2085                2090                2095

Ala Leu His Val Asp Val Asp Val Ser Ser Gly Phe Ile Tyr Trp Cys
            2100                2105                2110

Asp Phe Ser Ser Val Ala Ser Asp Asn Ala Ile Arg Arg Ile Lys
        2115                2120                2125

Pro Asp Gly Ser Ser Leu Met Asn Ile Val Thr His Gly Ile Gly Glu
        2130                2135                2140

Asn Gly Val Arg Gly Ile Ala Val Asp Trp Val Ala Gly Asn Leu Tyr
2145                2150                2155                2160

Phe Thr Asn Ala Phe Val Ser Glu Thr Leu Ile Glu Val Leu Arg Ile
                2165                2170                2175

Asn Thr Thr Tyr Arg Arg Val Leu Leu Lys Val Thr Val Asp Met Pro
            2180                2185                2190

Arg His Ile Val Val Asp Pro Lys Asn Arg Tyr Leu Phe Trp Ala Asp
            2195                2200                2205

Tyr Gly Gln Arg Pro Lys Ile Glu Arg Ser Phe Leu Asp Cys Thr Asn
        2210                2215                2220

Arg Thr Val Leu Val Ser Glu Gly Ile Val Thr Pro Arg Gly Leu Ala
2225                2230                2235                2240

Val Asp Arg Ser Asp Gly Tyr Val Tyr Trp Val Asp Asp Ser Leu Asp
            2245                2250                2255

Ile Ile Ala Arg Ile Arg Ile Asn Gly Glu Asn Ser Glu Val Ile Arg
            2260                2265                2270

Tyr Gly Ser Arg Tyr Pro Thr Pro Tyr Gly Ile Thr Val Phe Glu Asn
        2275                2280                2285

Ser Ile Ile Trp Val Asp Arg Asn Leu Lys Lys Ile Phe Gln Ala Ser
        2290                2295                2300

Lys Glu Pro Glu Asn Thr Glu Pro Pro Thr Val Ile Arg Asp Asn Ile
2305                2310                2315                2320

Asn Trp Leu Arg Asp Val Thr Ile Phe Asp Lys Gln Val Gln Pro Arg
            2325                2330                2335

Ser Pro Ala Glu Val Asn Asn Asn Pro Cys Leu Glu Asn Asn Gly Gly
        2340                2345                2350

Cys Ser His Leu Cys Phe Ala Leu Pro Gly Leu His Thr Pro Lys Cys
        2355                2360                2365

Asp Cys Ala Phe Gly Thr Leu Gln Ser Asp Gly Lys Asn Cys Ala Ile
2370                2375                2380

Ser Thr Glu Asn Phe Leu Ile Phe Ala Leu Ser Asn Ser Leu Arg Ser
2385                2390                2395                2400

Leu His Leu Asp Pro Glu Asn His Ser Pro Pro Phe Gln Thr Ile Asn
                2405                2410                2415

Val Glu Arg Thr Val Met Ser Leu Asp Tyr Asp Ser Val Ser Asp Arg
            2420                2425                2430

Ile Tyr Phe Thr Gln Asn Leu Ala Ser Gly Val Gly Gln Ile Ser Tyr
        2435                2440                2445

Ala Thr Leu Ser Ser Gly Ile His Thr Pro Thr Val Ile Ala Ser Gly
        2450                2455                2460

Ile Gly Thr Ala Asp Gly Ile Ala Phe Asp Trp Ile Thr Arg Arg Ile
2465                2470                2475                2480
```

```
Tyr Tyr Ser Asp Tyr Leu Asn Gln Met Ile Asn Ser Met Ala Glu Asp
            2485                2490                2495

Gly Ser Asn Arg Thr Val Ile Ala Arg Val Pro Lys Pro Arg Ala Ile
        2500                2505                2510

Val Leu Asp Pro Cys Gln Gly Tyr Leu Tyr Trp Ala Asp Trp Asp Thr
        2515                2520                2525

His Ala Lys Ile Glu Arg Ala Thr Leu Gly Gly Asn Phe Arg Val Pro
        2530                2535                2540

Ile Val Asn Ser Ser Leu Val Met Pro Ser Gly Leu Thr Leu Asp Tyr
2545                2550                2555                2560

Glu Glu Asp Leu Leu Tyr Trp Val Asp Ala Ser Leu Gln Arg Ile Glu
            2565                2570                2575

Arg Ser Thr Leu Thr Gly Val Asp Arg Glu Val Ile Val Asn Ala Ala
        2580                2585                2590

Val His Ala Phe Gly Leu Thr Leu Tyr Gly Gln Tyr Ile Tyr Trp Thr
        2595                2600                2605

Asp Leu Tyr Thr Gln Arg Ile Tyr Arg Ala Asn Lys Tyr Asp Gly Ser
        2610                2615                2620

Gly Gln Ile Ala Met Thr Thr Asn Leu Leu Ser Gln Pro Arg Gly Ile
2625                2630                2635                2640

Asn Thr Val Val Lys Asn Gln Lys Gln Cys Asn Asn Pro Cys Glu
            2645                2650                2655

Gln Phe Asn Gly Gly Cys Ser His Ile Cys Ala Pro Gly Pro Asn Gly
        2660                2665                2670

Ala Glu Cys Gln Cys Pro His Glu Gly Asn Trp Tyr Leu Ala Asn Asn
        2675                2680                2685

Arg Lys His Cys Ile Val Asp Asn Gly Glu Arg Cys Gly Ala Ser Ser
        2690                2695                2700

Phe Thr Cys Ser Asn Gly Arg Cys Ile Ser Glu Glu Trp Lys Cys Asp
2705                2710                2715                2720

Asn Asp Asn Asp Cys Gly Asp Gly Ser Asp Glu Met Glu Ser Val Cys
            2725                2730                2735

Ala Leu His Thr Cys Ser Pro Thr Ala Phe Thr Cys Ala Asn Gly Arg
        2740                2745                2750

Cys Val Gln Tyr Ser Tyr Arg Cys Asp Tyr Tyr Asn Asp Cys Gly Asp
        2755                2760                2765

Gly Ser Asp Glu Ala Gly Cys Leu Phe Arg Asp Cys Asn Ala Thr Thr
        2770                2775                2780

Glu Phe Met Cys Asn Asn Arg Arg Cys Ile Pro Arg Glu Phe Ile Cys
2785                2790                2795                2800

Asn Gly Val Asp Asn Cys His Asp Asn Asn Thr Ser Asp Glu Lys Asn
            2805                2810                2815

Cys Pro Asp Arg Thr Cys Gln Ser Gly Tyr Thr Lys Cys His Asn Ser
        2820                2825                2830

Asn Ile Cys Ile Pro Arg Val Tyr Leu Cys Asp Gly Asp Asn Asp Cys
        2835                2840                2845

Gly Asp Asn Ser Asp Glu Asn Pro Thr Tyr Cys Thr Thr His Thr Cys
        2850                2855                2860

Ser Ser Ser Glu Phe Gln Cys Ala Ser Gly Arg Cys Ile Pro Gln His
2865                2870                2875                2880

Trp Tyr Cys Asp Gln Glu Thr Asp Cys Phe Asp Ala Ser Asp Glu Pro
            2885                2890                2895
```

-continued

```
Ala Ser Cys Gly His Ser Glu Arg Thr Cys Leu Ala Asp Glu Phe Lys
        2900                2905                2910
Cys Asp Gly Gly Arg Cys Ile Pro Ser Glu Trp Ile Cys Asp Gly Asp
    2915                2920                2925
Asn Asp Cys Gly Asp Met Ser Asp Glu Asp Lys Arg His Gln Cys Gln
    2930                2935                2940
Asn Gln Asn Cys Ser Asp Ser Glu Phe Leu Cys Val Asn Asp Arg Pro
2945                2950                2955                2960
Pro Asp Arg Arg Cys Ile Pro Gln Ser Trp Val Cys Asp Gly Asp Val
            2965                2970                2975
Asp Cys Thr Asp Gly Tyr Asp Glu Asn Gln Asn Cys Thr Arg Arg Thr
        2980                2985                2990
Cys Ser Glu Asn Glu Phe Thr Cys Gly Tyr Gly Leu Cys Ile Pro Lys
    2995                3000                3005
Ile Phe Arg Cys Asp Arg His Asn Asp Cys Gly Asp Tyr Ser Asp Glu
    3010                3015                3020
Arg Gly Cys Leu Tyr Gln Thr Cys Gln Gln Asn Gln Phe Thr Cys Gln
3025                3030                3035                3040
Asn Gly Arg Cys Ile Ser Lys Thr Phe Val Cys Asp Glu Asp Asn Asp
            3045                3050                3055
Cys Gly Asp Gly Ser Asp Glu Leu Met His Leu Cys His Thr Pro Glu
        3060                3065                3070
Pro Thr Cys Pro Pro His Glu Phe Lys Cys Asp Asn Gly Arg Cys Ile
    3075                3080                3085
Glu Met Met Lys Leu Cys Asn His Leu Asp Asp Cys Leu Asp Asn Ser
    3090                3095                3100
Asp Glu Lys Gly Cys Gly Ile Asn Glu Cys His Asp Pro Ser Ile Ser
3105                3110                3115                3120
Gly Cys Asp His Asn Cys Thr Asp Thr Leu Thr Ser Phe Tyr Cys Ser
            3125                3130                3135
Cys Arg Pro Gly Tyr Lys Leu Met Ser Asp Lys Arg Thr Cys Val Asp
        3140                3145                3150
Ile Asp Glu Cys Thr Glu Met Pro Phe Val Cys Ser Gln Lys Cys Glu
    3155                3160                3165
Asn Val Ile Gly Ser Tyr Ile Cys Lys Cys Ala Pro Gly Tyr Leu Arg
    3170                3175                3180
Glu Pro Asp Gly Lys Thr Cys Arg Gln Asn Ser Asn Ile Glu Pro Tyr
3185                3190                3195                3200
Leu Ile Phe Ser Asn Arg Tyr Tyr Leu Arg Asn Leu Thr Ile Asp Gly
            3205                3210                3215
Tyr Phe Tyr Ser Leu Ile Leu Glu Gly Leu Asp Asn Val Val Ala Leu
        3220                3225                3230
Asp Phe Asp Arg Val Glu Lys Arg Leu Tyr Trp Ile Asp Thr Gln Arg
    3235                3240                3245
Gln Val Ile Glu Arg Met Phe Leu Asn Lys Thr Asn Lys Glu Thr Ile
    3250                3255                3260
Ile Asn His Arg Leu Pro Ala Ala Glu Ser Leu Ala Val Asp Trp Val
3265                3270                3275                3280
Ser Arg Lys Leu Tyr Trp Leu Asp Ala Arg Leu Asp Gly Leu Phe Val
            3285                3290                3295
Ser Asp Leu Asn Gly Gly His Arg Arg Met Leu Ala Gln His Cys Val
        3300                3305                3310
Asp Ala Asn Asn Thr Phe Cys Phe Asp Asn Pro Arg Gly Leu Ala Leu
```

```
                3315                3320                3325
His Pro Gln Tyr Gly Tyr Leu Tyr Trp Ala Asp Trp Gly His Arg Ala
    3330                3335                3340
Tyr Ile Gly Arg Val Gly Met Asp Gly Thr Asn Lys Ser Val Ile Ile
3345                3350                3355                3360
Ser Thr Lys Leu Glu Trp Pro Asn Gly Ile Thr Ile Asp Tyr Thr Asn
            3365                3370                3375
Asp Leu Leu Tyr Trp Ala Asp Ala His Leu Gly Tyr Ile Glu Tyr Ser
        3380                3385                3390
Asp Leu Glu Gly His His Arg His Thr Val Tyr Asp Gly Ala Leu Pro
    3395                3400                3405
His Pro Phe Ala Ile Thr Ile Phe Glu Asp Thr Ile Tyr Trp Thr Asp
    3410                3415                3420
Trp Asn Thr Arg Thr Val Glu Lys Gly Asn Lys Tyr Asp Gly Ser Asn
3425                3430                3435                3440
Arg Gln Thr Leu Val Asn Thr Thr His Arg Pro Phe Asp Ile His Val
            3445                3450                3455
Tyr His Pro Tyr Arg Gln Pro Ile Val Ser Asn Pro Cys Gly Thr Asn
        3460                3465                3470
Asn Gly Gly Cys Ser His Leu Cys Leu Ile Lys Pro Gly Gly Lys Gly
        3475                3480                3485
Phe Thr Cys Glu Cys Pro Asp Asp Phe Arg Thr Leu Gln Leu Ser Gly
        3490                3495                3500
Ser Thr Tyr Cys Met Pro Met Cys Ser Ser Thr Gln Phe Leu Cys Ala
3505                3510                3515                3520
Asn Asn Glu Lys Cys Ile Pro Ile Trp Trp Lys Cys Asp Gly Gln Lys
            3525                3530                3535
Asp Cys Ser Asp Gly Ser Asp Glu Leu Ala Leu Cys Pro Gln Arg Phe
        3540                3545                3550
Cys Arg Leu Gly Gln Phe Gln Cys Ser Asp Gly Asn Cys Thr Ser Pro
        3555                3560                3565
Gln Thr Leu Cys Asn Ala His Gln Asn Cys Pro Asp Gly Ser Asp Glu
    3570                3575                3580
Asp Arg Leu Leu Cys Glu Asn His His Cys Asp Ser Asn Glu Trp Gln
3585                3590                3595                3600
Cys Ala Asn Lys Arg Cys Ile Pro Glu Ser Trp Gln Cys Asp Thr Phe
            3605                3610                3615
Asn Asp Cys Glu Asp Asn Ser Asp Glu Asp Ser Ser His Cys Ala Ser
        3620                3625                3630
Arg Thr Cys Arg Pro Gly Gln Phe Arg Cys Ala Asn Gly Arg Cys Ile
        3635                3640                3645
Pro Gln Ala Trp Lys Cys Asp Val Asp Asn Asp Cys Gly Asp His Ser
    3650                3655                3660
Asp Glu Pro Ile Glu Glu Cys Met Ser Ser Ala His Leu Cys Asp Asn
3665                3670                3675                3680
Phe Thr Glu Phe Ser Cys Lys Thr Asn Tyr Arg Cys Ile Pro Lys Trp
            3685                3690                3695
Ala Val Cys Asn Gly Val Asp Asp Cys Arg Asp Asn Ser Asp Glu Gln
        3700                3705                3710
Gly Cys Glu Glu Arg Thr Cys His Pro Val Gly Asp Phe Arg Cys Lys
        3715                3720                3725
Asn His His Cys Ile Pro Leu Arg Trp Gln Cys Asp Gly Gln Asn Asp
    3730                3735                3740
```

-continued

```
Cys Gly Asp Asn Ser Asp Glu Glu Asn Cys Ala Pro Arg Glu Cys Thr
3745                3750                3755                3760

Glu Ser Glu Phe Arg Cys Val Asn Gln Gln Cys Ile Pro Ser Arg Trp
            3765                3770                3775

Ile Cys Asp His Tyr Asn Asp Cys Gly Asp Asn Ser Asp Glu Arg Asp
        3780                3785                3790

Cys Glu Met Arg Thr Cys His Pro Glu Tyr Phe Gln Cys Thr Ser Gly
    3795                3800                3805

His Cys Val His Ser Glu Leu Lys Cys Asp Gly Ser Ala Asp Cys Leu
3810                3815                3820

Asp Ala Ser Asp Glu Ala Asp Cys Pro Thr Arg Phe Pro Asp Gly Ala
3825                3830                3835                3840

Tyr Cys Gln Ala Thr Met Phe Glu Cys Lys Asn His Val Cys Ile Pro
            3845                3850                3855

Pro Tyr Trp Lys Cys Asp Gly Asp Asp Asp Cys Gly Asp Gly Ser Asp
        3860                3865                3870

Glu Glu Leu His Leu Cys Leu Asp Val Pro Cys Asn Ser Pro Asn Arg
    3875                3880                3885

Phe Arg Cys Asp Asn Asn Arg Cys Ile Tyr Ser His Glu Val Cys Asn
3890                3895                3900

Gly Val Asp Asp Cys Gly Asp Gly Thr Asp Glu Thr Glu Glu His Cys
3905                3910                3915                3920

Arg Lys Pro Thr Pro Lys Pro Cys Thr Glu Tyr Glu Tyr Lys Cys Gly
            3925                3930                3935

Asn Gly His Cys Ile Pro His Asp Asn Val Cys Asp Asp Ala Asp Asp
        3940                3945                3950

Cys Gly Asp Trp Ser Asp Glu Leu Gly Cys Asn Lys Gly Lys Glu Arg
    3955                3960                3965

Thr Cys Ala Glu Asn Ile Cys Glu Gln Asn Cys Thr Gln Leu Asn Glu
    3970                3975                3980

Gly Gly Phe Ile Cys Ser Cys Thr Ala Gly Phe Glu Thr Asn Val Phe
3985                3990                3995                4000

Asp Arg Thr Ser Cys Leu Asp Ile Asn Glu Cys Glu Gln Phe Gly Thr
            4005                4010                4015

Cys Pro Gln His Cys Arg Asn Thr Lys Gly Ser Tyr Glu Cys Val Cys
        4020                4025                4030

Ala Asp Gly Phe Thr Ser Met Ser Asp Arg Pro Gly Lys Arg Cys Ala
    4035                4040                4045

Ala Glu Gly Ser Ser Pro Leu Leu Leu Leu Pro Asp Asn Val Arg Ile
    4050                4055                4060

Arg Lys Tyr Asn Leu Ser Ser Glu Arg Phe Ser Glu Tyr Leu Gln Asp
4065                4070                4075                4080

Glu Glu Tyr Ile Gln Ala Val Asp Tyr Asp Trp Asp Pro Lys Asp Ile
            4085                4090                4095

Gly Leu Ser Val Val Tyr Tyr Thr Val Arg Gly Glu Gly Ser Arg Phe
        4100                4105                4110

Gly Ala Ile Lys Arg Ala Tyr Ile Pro Asn Phe Glu Ser Gly Arg Asn
    4115                4120                4125

Asn Leu Val Gln Glu Val Asp Leu Lys Leu Lys Tyr Val Met Gln Pro
    4130                4135                4140

Asp Gly Ile Ala Val Asp Trp Val Gly Arg His Ile Tyr Trp Ser Asp
4145                4150                4155                4160
```

-continued

Val Lys Asn Lys Arg Ile Glu Val Ala Lys Leu Asp Gly Arg Tyr Arg
            4165                4170                4175

Lys Trp Leu Ile Ser Thr Asp Leu Asp Gln Pro Ala Ala Ile Ala Val
        4180                4185                4190

Asn Pro Lys Leu Gly Leu Met Phe Trp Thr Asp Trp Gly Lys Glu Pro
    4195                4200                4205

Lys Ile Glu Ser Ala Trp Met Asn Gly Glu Asp Arg Asn Ile Leu Val
    4210                4215                4220

Phe Glu Asp Leu Gly Trp Pro Thr Gly Leu Ser Ile Asp Tyr Leu Asn
4225                4230                4235                4240

Asn Asp Arg Ile Tyr Trp Ser Asp Phe Lys Glu Asp Val Ile Glu Thr
            4245                4250                4255

Ile Lys Tyr Asp Gly Thr Asp Arg Arg Val Ile Ala Lys Glu Ala Met
        4260                4265                4270

Asn Pro Tyr Ser Leu Asp Ile Phe Glu Asp Gln Leu Tyr Trp Ile Ser
    4275                4280                4285

Lys Glu Lys Gly Glu Val Trp Lys Gln Asn Lys Phe Gly Gln Gly Lys
    4290                4295                4300

Lys Glu Lys Thr Leu Val Val Asn Pro Trp Leu Thr Gln Val Arg Ile
4305                4310                4315                4320

Phe His Gln Leu Arg Tyr Asn Lys Ser Val Pro Asn Leu Cys Lys Gln
            4325                4330                4335

Ile Cys Ser His Leu Cys Leu Leu Arg Pro Gly Gly Tyr Ser Cys Ala
        4340                4345                4350

Cys Pro Gln Gly Ser Ser Phe Ile Glu Gly Ser Thr Thr Glu Cys Asp
    4355                4360                4365

Ala Ala Ile Glu Leu Pro Ile Asn Leu Pro Pro Pro Cys Arg Cys Met
    4370                4375                4380

His Gly Gly Asn Cys Tyr Phe Asp Glu Thr Asp Leu Pro Lys Cys Lys
4385                4390                4395                4400

Cys Pro Ser Gly Tyr Thr Gly Lys Tyr Cys Glu Met Ala Phe Ser Lys
            4405                4410                4415

Gly Ile Ser Pro Gly Thr Thr Ala Val Ala Val Leu Leu Thr Ile Leu
        4420                4425                4430

Leu Ile Val Val Ile Gly Ala Leu Ala Ile Ala Gly Phe Phe His Tyr
    4435                4440                4445

Arg Arg Thr Gly Ser Leu Leu Pro Ala Leu Pro Lys Leu Pro Ser Leu
    4450                4455                4460

Ser Ser Leu Val Lys Pro Ser Glu Asn Gly Asn Gly Val Thr Phe Arg
4465                4470                4475                4480

Ser Gly Ala Asp Leu Asn Met Asp Ile Gly Val Ser Gly Phe Gly Pro
            4485                4490                4495

Glu Thr Ala Ile Asp Arg Ser Met Ala Met Ser Glu Asp Phe Val Met
        4500                4505                4510

Glu Met Gly Lys Gln Pro Ile Ile Phe Glu Asn Pro Met Tyr Ser Ala
    4515                4520                4525

Arg Asp Ser Ala Val Lys Val Val Gln Pro Ile Gln Val Thr Val Ser
    4530                4535                4540

Glu Asn Val Asp Asn Lys Asn Tyr Gly Ser Pro Ile Asn Pro Ser Glu
4545                4550                4555                4560

Ile Val Pro Glu Thr Asn Pro Thr Ser Pro Ala Ala Asp Gly Thr Gln
            4565                4570                4575

Val Thr Lys Trp Asn Leu Phe Lys Arg Lys Ser Lys Gln Thr Thr Asn

-continued

```
                  4580                4585                4590
Phe Glu Asn Pro Ile Tyr Ala Gln Met Glu Asn Glu Gln Lys Glu Ser
        4595                4600                4605

Val Ala Ala Thr Pro Pro Pro Ser Pro Ser Leu Pro Ala Lys Pro Lys
    4610                4615                4620

Pro Pro Ser Arg Arg Asp Pro Thr Pro Thr Tyr Ser Ala Thr Glu Asp
4625            4630                4635                4640

Thr Phe Lys Asp Thr Ala Asn Leu Val Lys Glu Asp Ser Glu Val
            4645                4650                4655
```